US009850545B2

(12) United States Patent
Petrauskene et al.

(10) Patent No.: US 9,850,545 B2
(45) Date of Patent: Dec. 26, 2017

(54) MULTI-PRIMER ASSAY FOR *MYCOPLASMA* DETECTION

(71) Applicant: LIFE TECHNOLOGIES CORPORATION, Carlsbad, CA (US)

(72) Inventors: Olga Petrauskene, San Carlos, CA (US); Pius Brzoska, Woodside, CA (US); Somaya Bit, San Ramon, CA (US); Jen-Kuei Liu, Palo Alto, CA (US); Robert Tebbs, Austin, TX (US); Manohar Furtado, San Ramon, CA (US)

(73) Assignee: Life Technologies Corporation, Carlsbad, CA (US)

( * ) Notice: Subject to any disclaimer, the term of this patent is extended or adjusted under 35 U.S.C. 154(b) by 503 days.

(21) Appl. No.: 14/314,985

(22) Filed: Jun. 25, 2014

(65) Prior Publication Data
US 2014/0378330 A1    Dec. 25, 2014

Related U.S. Application Data

(63) Continuation of application No. 12/916,420, filed on Oct. 29, 2010, now abandoned.

(60) Provisional application No. 61/262,492, filed on Nov. 18, 2009, provisional application No. 61/256,413, filed on Oct. 30, 2009.

(51) Int. Cl.
*C12Q 1/68*    (2006.01)
(52) U.S. Cl.
CPC ......... *C12Q 1/689* (2013.01); *C12Q 2600/16* (2013.01)
(58) Field of Classification Search
None
See application file for complete search history.

(56) References Cited

U.S. PATENT DOCUMENTS

| 5,491,062 | A | 2/1996 | Mckenzie et al. | |
|---|---|---|---|---|
| 6,262,333 | B1 * | 7/2001 | Endege | C07K 14/47 435/320.1 |
| 6,492,113 | B1 * | 12/2002 | Vojdani | C12Q 1/689 435/15 |
| 6,569,627 | B2 | 5/2003 | Wittwer | |
| 7,408,051 | B2 * | 8/2008 | Ma | C07H 21/04 435/6.12 |
| 7,955,802 | B2 * | 6/2011 | Whitman | C12Q 1/6818 435/6.12 |
| 9,212,397 | B2 * | 12/2015 | Kaplan | C12Q 1/689 |
| 2004/0077015 | A1 | 4/2004 | Vojdani | |
| 2008/0187916 | A1 | 8/2008 | Ikonomi et al. | |
| 2008/0233570 | A1 | 9/2008 | Hall et al. | |
| 2009/0053703 | A1 | 2/2009 | Bergeron et al. | |
| 2009/0075273 | A1 | 3/2009 | Slepnev et al. | |
| 2009/0181368 | A1 | 7/2009 | Iwakiri | |
| 2010/0323362 | A1 | 12/2010 | Kaplan et al. | |

FOREIGN PATENT DOCUMENTS

| JP | WO2007114518 | * 10/2007 | ............... C12Q 1/68 |
|---|---|---|---|
| WO | WO-2007/114518 A1 | 10/2007 | |

OTHER PUBLICATIONS

Pettersson et al. (Appl. Environ. Microbiol. 1994, 60 (7), 2456-2461).*
Yoshida et al. (J. Clin. Microbiol., 2002, 40 (1), 105-110).*
Lowe et al. (Nucleic Acids Research, 1990, 18(7):1757-1761).*
Welti et al. (Diagnostic Microbiology and Infectious Disease, 2003, vol. 45, p. 85-95).*
Gruteke, P. et al., "PracticalImplemenlation of a MultiplexPCR for Acute Respiratory Tract Infections in Children", *J. Clin. Microbiol*, vol. 42, (12), 2004, 5596-5603.
Lowe, T. et al., "A Computer Program for Selection of Oligonucleotide Primers for Polymerase Chain Reactions", *Nucleic Acids Research*, vol. 18(7), 1990, 1757-1761.
PCT/US10/54867, , "International Search Report & Written Opinion dated Jun. 6, 2011", 25 Pgs.
PCT/US2010/054867, "International Preliminary Report on Patentability dated May 1, 2012", dated May 1, 2012, 1-8.
Pettersson, B. et al., "Sequence Analysis of 16S rRNA from Mycoplasmas by Direct Solid-Phase DNA Sequencing", *Appl. Environ. Microbiol.*, vol. 60 (7), Jul. 1994, 2456-2461.
Wang, H. et al., "Multiplex PCR for avian pathogenic mycoplasmas", *Molecular and Cellular Probes*, vol. 11, 1997, 211-216.
Welti, M. et al., "Development of a multiplex real-time quantitative peR assay to detect", *Diagnostic Microbiology and Infectious Disease*, vol. 45, 2003, 85-95.
Yoshida, T. et al., "Phylogeny-Based Rapid Identification of Mycoplasmas and Ureaplasmas from Urethritis Patients", *J. Clin. Microbiol.*, vol. 40 (1), Jan. 2002, 105-110.

* cited by examiner

*Primary Examiner* — Stephanie K Mummert
(74) *Attorney, Agent, or Firm* — Daphne Reddy

(57) ABSTRACT

Disclosed is a multi-primer amplification assay, method and kits for detecting *Mycoplasma* species and closely related species utilizing a plurality of oligonucleotide primers in contact with a sample in a single vessel and detecting the amplification product, wherein the presence of an amplification product indicates *Mycoplasma* in the sample.

19 Claims, 4 Drawing Sheets

Fig. 4A | Fig. 4B
--------------------Positive--------------------
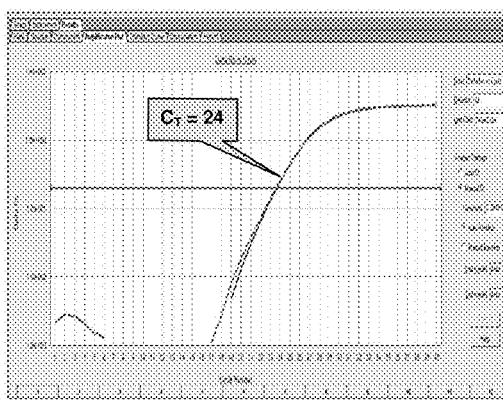 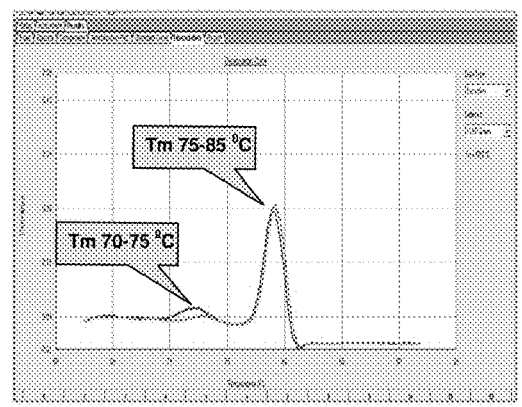
Fig. 4C | Fig. 4D
--------------------Negative--------------------
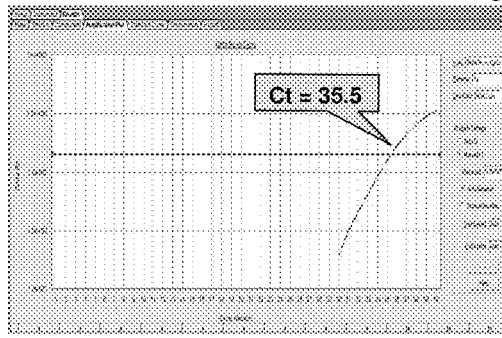 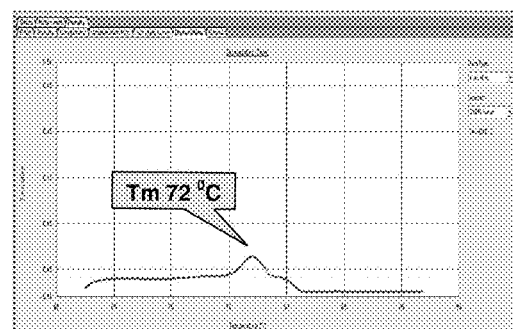
Fig. 4E | Fig. 4F
--------------------Positive--------------------
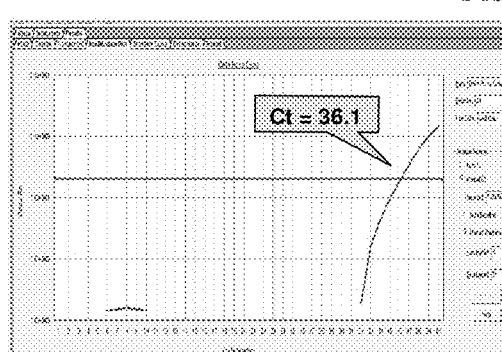 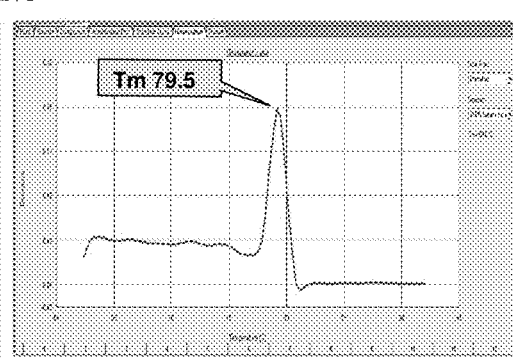

SEQUENCE LISTING

<160> NUMBER OF SEQ ID NOS: 144

<210> SEQ ID NO 1
<211> LENGTH: 24
<212> TYPE: DNA

```
<213> ORGANISM: Artificial Sequence
<220> FEATURE:
<223> OTHER INFORMATION: synthetic primer

<400> SEQUENCE: 1
gctgggtcta tactgacact gatg                                              24

<210> SEQ ID NO 2
<211> LENGTH: 22
<212> TYPE: DNA
<213> ORGANISM: Artificial Sequence
<220> FEATURE:
<223> OTHER INFORMATION: synthetic primer

<400> SEQUENCE: 2
gcttgctggg tctatactga ca                                                22

<210> SEQ ID NO 3
<211> LENGTH: 22
<212> TYPE: DNA
<213> ORGANISM: Artificial Sequence
<220> FEATURE:
<223> OTHER INFORMATION: synthetic primer

<400> SEQUENCE: 3
gcttgctggg tctatactga ca                                                22

<210> SEQ ID NO 4
<211> LENGTH: 24
<212> TYPE: DNA
<213> ORGANISM: Artificial Sequence
<220> FEATURE:
<223> OTHER INFORMATION: synthetic primer

<400> SEQUENCE: 4
ggcagctaac tgggaacata ttga                                              24

<210> SEQ ID NO 5
<211> LENGTH: 24
<212> TYPE: DNA
<213> ORGANISM: Artificial Sequence
<220> FEATURE:
<223> OTHER INFORMATION: synthetic primer

<400> SEQUENCE: 5
ggcgaaaact taggccatta ctga                                              24

<210> SEQ ID NO 6
<211> LENGTH: 23
<212> TYPE: DNA
<213> ORGANISM: Artificial Sequence
<220> FEATURE:
<223> OTHER INFORMATION: synthetic primer

<400> SEQUENCE: 6
ggtagagagt cctggaactc cat                                               23

<210> SEQ ID NO 7
<211> LENGTH: 22
<212> TYPE: DNA
<213> ORGANISM: Artificial Sequence
<220> FEATURE:
<223> OTHER INFORMATION: synthetic primer

<400> SEQUENCE: 7
ggttaaagtc cggagctcaa ct                                                22
```

<210> SEQ ID NO 8
<211> LENGTH: 24
<212> TYPE: DNA
<213> ORGANISM: Artificial Sequence
<220> FEATURE:
<223> OTHER INFORMATION: synthetic primer

<400> SEQUENCE: 8
gtagagagtc ctggaactcc atgt                                          24

<210> SEQ ID NO 9
<211> LENGTH: 25
<212> TYPE: DNA
<213> ORGANISM: Artificial Sequence
<220> FEATURE:
<223> OTHER INFORMATION: synthetic primer

<400> SEQUENCE: 9
tgtggtaggg agttttggaa tttca                                         25

<210> SEQ ID NO 10
<211> LENGTH: 26
<212> TYPE: DNA
<213> ORGANISM: Artificial Sequence
<220> FEATURE:
<223> OTHER INFORMATION: synthetic primer

<400> SEQUENCE: 10
cagctaactg ggaacatatt gacact                                        26

<210> SEQ ID NO 11
<211> LENGTH: 19
<212> TYPE: DNA
<213> ORGANISM: Artificial Sequence
<220> FEATURE:
<223> OTHER INFORMATION: synthetic primer

<400> SEQUENCE: 11
cgaaggcagc ttactgggt                                                19

<210> SEQ ID NO 12
<211> LENGTH: 25
<212> TYPE: DNA
<213> ORGANISM: Artificial Sequence
<220> FEATURE:
<223> OTHER INFORMATION: synthetic primer

<400> SEQUENCE: 12
cggttttgca agtttgaggt taaag                                         25

<210> SEQ ID NO 13
<211> LENGTH: 22
<212> TYPE: DNA
<213> ORGANISM: Artificial Sequence
<220> FEATURE:
<223> OTHER INFORMATION: synthetic primer

<400> SEQUENCE: 13
gaaggcagct tactgggtct at                                            22

<210> SEQ ID NO 14
<211> LENGTH: 22
<212> TYPE: DNA
<213> ORGANISM: Artificial Sequence
<220> FEATURE:

```
<223> OTHER INFORMATION: synthetic primer

<400> SEQUENCE: 14
gaaggcagct tactgggtct at                                            22

<210> SEQ ID NO 15
<211> LENGTH: 24
<212> TYPE: DNA
<213> ORGANISM: Artificial Sequence
<220> FEATURE:
<223> OTHER INFORMATION: synthetic primer

<400> SEQUENCE: 15
gaaggcgaaa acttaggcca ttac                                          24

<210> SEQ ID NO 16
<211> LENGTH: 25
<212> TYPE: DNA
<213> ORGANISM: Artificial Sequence
<220> FEATURE:
<223> OTHER INFORMATION: synthetic primer

<400> SEQUENCE: 16
gcagctaact gggaacatat tgaca                                         25

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
gcgaaggcag ctaactggtt                                               20

<210> SEQ ID NO 18
<211> LENGTH: 23
<212> TYPE: DNA
<213> ORGANISM: Artificial Sequence
<220> FEATURE:
<223> OTHER INFORMATION: synthetic primer

<400> SEQUENCE: 18
gcgaaggcag ctaactggtt ata                                           23

<210> SEQ ID NO 19
<211> LENGTH: 18
<212> TYPE: DNA
<213> ORGANISM: Artificial Sequence
<220> FEATURE:
<223> OTHER INFORMATION: synthetic primer

<400> SEQUENCE: 19
gcgaaggcga ggacttgg                                                 18

<210> SEQ ID NO 20
<211> LENGTH: 22
<212> TYPE: DNA
<213> ORGANISM: Artificial Sequence
<220> FEATURE:
<223> OTHER INFORMATION: synthetic primer

<400> SEQUENCE: 20
gcggttttgc aagtttgagg tt                                            22
```

```
<210> SEQ ID NO 21
<211> LENGTH: 25
<212> TYPE: DNA
<213> ORGANISM: Artificial Sequence
<220> FEATURE:
<223> OTHER INFORMATION: synthetic primer

<400> SEQUENCE: 21
gaacgggtga gtaacacgta tctaa                                          25

<210> SEQ ID NO 22
<211> LENGTH: 22
<212> TYPE: DNA
<213> ORGANISM: Artificial Sequence
<220> FEATURE:
<223> OTHER INFORMATION: synthetic primer

<400> SEQUENCE: 22
gaaggcagct aactggttat at                                             22

<210> SEQ ID NO 23
<211> LENGTH: 26
<212> TYPE: DNA
<213> ORGANISM: Artificial Sequence
<220> FEATURE:
<223> OTHER INFORMATION: synthetic primer

<400> SEQUENCE: 23
gtggagcatg tggtttaatt tgaaga                                         26

<210> SEQ ID NO 24
<211> LENGTH: 26
<212> TYPE: DNA
<213> ORGANISM: Artificial Sequence
<220> FEATURE:
<223> OTHER INFORMATION: synthetic primer

<400> SEQUENCE: 24
gtggagcatg ttgcttaatt cgacgg                                         26

<210> SEQ ID NO 25
<211> LENGTH: 26
<212> TYPE: DNA
<213> ORGANISM: Artificial Sequence
<220> FEATURE:
<223> OTHER INFORMATION: synthetic primer

<400> SEQUENCE: 25
gtggagcatg tggtttaatt tgaaga                                         26

<210> SEQ ID NO 26
<211> LENGTH: 26
<212> TYPE: DNA
<213> ORGANISM: Artificial Sequence
<220> FEATURE:
<223> OTHER INFORMATION: synthetic primer

<400> SEQUENCE: 26
gtggagcatg tggtttaatt tgaaga                                         26

<210> SEQ ID NO 27
<211> LENGTH: 25
<212> TYPE: DNA
<213> ORGANISM: Artificial Sequence
<220> FEATURE:
<223> OTHER INFORMATION: synthetic primer
```

```
<400> SEQUENCE: 27
cgcaacccct gtccttagtt acttt                                            25

<210> SEQ ID NO 28
<211> LENGTH: 25
<212> TYPE: DNA
<213> ORGANISM: Artificial Sequence
<220> FEATURE:
<223> OTHER INFORMATION: synthetic primer

<400> SEQUENCE: 28
cgcaacccct attgctagtt accat                                            25

<210> SEQ ID NO 29
<211> LENGTH: 24
<212> TYPE: DNA
<213> ORGANISM: Artificial Sequence
<220> FEATURE:
<223> OTHER INFORMATION: synthetic primer

<400> SEQUENCE: 29
gcagctaact gggaacatat tgac                                             24

<210> SEQ ID NO 30
<211> LENGTH: 28
<212> TYPE: DNA
<213> ORGANISM: Artificial Sequence
<220> FEATURE:
<223> OTHER INFORMATION: synthetic primer

<400> SEQUENCE: 30
cgcaacccct gtccttagtt actttatc                                         28

<210> SEQ ID NO 31
<211> LENGTH: 28
<212> TYPE: DNA
<213> ORGANISM: Artificial Sequence
<220> FEATURE:
<223> OTHER INFORMATION: synthetic primer

<400> SEQUENCE: 31
cgcaacccct gccgttagtt actccatt                                         28

<210> SEQ ID NO 32
<211> LENGTH: 18
<212> TYPE: DNA
<213> ORGANISM: Artificial Sequence
<220> FEATURE:
<223> OTHER INFORMATION: synthetic primer

<400> SEQUENCE: 32
gacagatggt gcatggtt                                                    18

<210> SEQ ID NO 33
<211> LENGTH: 18
<212> TYPE: DNA
<213> ORGANISM: Artificial Sequence
<220> FEATURE:
<223> OTHER INFORMATION: synthetic primer

<400> SEQUENCE: 33
gacagatggt gcatggtt                                                    18

<210> SEQ ID NO 34
<211> LENGTH: 19
```

<212> TYPE: DNA
<213> ORGANISM: Artificial Sequence
<220> FEATURE:
<223> OTHER INFORMATION: synthetic primer

<400> SEQUENCE: 34
gacagatggt gcatggtta                                               19

<210> SEQ ID NO 35
<211> LENGTH: 19
<212> TYPE: DNA
<213> ORGANISM: Artificial Sequence
<220> FEATURE:
<223> OTHER INFORMATION: synthetic primer

<400> SEQUENCE: 35
gacagatggt gcatggttt                                               19

<210> SEQ ID NO 36
<211> LENGTH: 19
<212> TYPE: DNA
<213> ORGANISM: Artificial Sequence
<220> FEATURE:
<223> OTHER INFORMATION: synthetic primer

<400> SEQUENCE: 36
gacagatggt gcatggttc                                               19

<210> SEQ ID NO 37
<211> LENGTH: 19
<212> TYPE: DNA
<213> ORGANISM: Artificial Sequence
<220> FEATURE:
<223> OTHER INFORMATION: synthetic primer

<400> SEQUENCE: 37
gacagatggt gcatggttg                                               19

<210> SEQ ID NO 38
<211> LENGTH: 18
<212> TYPE: DNA
<213> ORGANISM: Artificial Sequence
<220> FEATURE:
<223> OTHER INFORMATION: synthetic primer

<400> SEQUENCE: 38
gacaggtggt gcatggtt                                                18

<210> SEQ ID NO 39
<211> LENGTH: 18
<212> TYPE: DNA
<213> ORGANISM: Artificial Sequence
<220> FEATURE:
<223> OTHER INFORMATION: synthetic primer

<400> SEQUENCE: 39
gacaggtggt gcatggtt                                                18

<210> SEQ ID NO 40
<211> LENGTH: 18
<212> TYPE: DNA
<213> ORGANISM: Artificial Sequence
<220> FEATURE:
<223> OTHER INFORMATION: synthetic primer

<400> SEQUENCE: 40
tacaggtggt gcacggtt                           18

<210> SEQ ID NO 41
<211> LENGTH: 23
<212> TYPE: DNA
<213> ORGANISM: Artificial Sequence
<220> FEATURE:
<223> OTHER INFORMATION: synthetic primer

<400> SEQUENCE: 41
agatacgcgt agaaccttac cca                     23

<210> SEQ ID NO 42
<211> LENGTH: 23
<212> TYPE: DNA
<213> ORGANISM: Artificial Sequence
<220> FEATURE:
<223> OTHER INFORMATION: synthetic primer

<400> SEQUENCE: 42
cggtacacga aaaccttac cta                      23

<210> SEQ ID NO 43
<211> LENGTH: 23
<212> TYPE: DNA
<213> ORGANISM: Artificial Sequence
<220> FEATURE:
<223> OTHER INFORMATION: synthetic primer

<400> SEQUENCE: 43
agatacgcgg agaaccttac cca                     23

<210> SEQ ID NO 44
<211> LENGTH: 23
<212> TYPE: DNA
<213> ORGANISM: Artificial Sequence
<220> FEATURE:
<223> OTHER INFORMATION: synthetic primer

<400> SEQUENCE: 44
agatacgcgg agaaccttac cca                     23

<210> SEQ ID NO 45
<211> LENGTH: 25
<212> TYPE: DNA
<213> ORGANISM: Artificial Sequence
<220> FEATURE:
<223> OTHER INFORMATION: synthetic primer

<400> SEQUENCE: 45 cgcaacccctt gtccttagtt acttt                  25

<210> SEQ ID NO 46
<211> LENGTH: 25
<212> TYPE: DNA
<213> ORGANISM: Artificial Sequence
<220> FEATURE:
<223> OTHER INFORMATION: synthetic primer

<400> SEQUENCE: 46 cgcaacccctt gccgttagtt actcc                  25

<210> SEQ ID NO 47
<211> LENGTH: 24
<212> TYPE: DNA
<213> ORGANISM: Artificial Sequence
<220> FEATURE:
<223> OTHER INFORMATION: synthetic primer

<400> SEQUENCE: 47
cgaatgggtg agtaacacgt actt                                              24

<210> SEQ ID NO 48
<211> LENGTH: 24
<212> TYPE: DNA
<213> ORGANISM: Artificial Sequence
<220> FEATURE:
<223> OTHER INFORMATION: synthetic primer

<400> SEQUENCE: 48
cgaatgggtg agtaacacgt gctt                                              24

<210> SEQ ID NO 49
<211> LENGTH: 24
<212> TYPE: DNA
<213> ORGANISM: Artificial Sequence
<220> FEATURE:
<223> OTHER INFORMATION: synthetic primer

<400> SEQUENCE: 49
cgaacgggtg agtaacacgt atct                                              24

<210> SEQ ID NO 50
<211> LENGTH: 24
<212> TYPE: DNA
<213> ORGANISM: Artificial Sequence
<220> FEATURE:
<223> OTHER INFORMATION: synthetic primer

<400> SEQUENCE: 50
ggcagctaac tggtttatata ttga                                             24

<210> SEQ ID NO 51
<211> LENGTH: 24
<212> TYPE: DNA
<213> ORGANISM: Artificial Sequence
<220> FEATURE:
<223> OTHER INFORMATION: synthetic primer

<400> SEQUENCE: 51
gtagagagtt ctggaactcc atgt                                              24

<210> SEQ ID NO 52
<211> LENGTH: 25
<212> TYPE: DNA
<213> ORGANISM: Artificial Sequence
<220> FEATURE:
<223> OTHER INFORMATION: synthetic primer

<400> SEQUENCE: 52
tgtggtagag agttctggaa ctcca                                             25

<210> SEQ ID NO 53
<211> LENGTH: 22
<212> TYPE: DNA
<213> ORGANISM: Artificial Sequence
<220> FEATURE:
<223> OTHER INFORMATION: synthetic primer

<400> SEQUENCE: 53
gcggttttgc aagtttgagg tt                                                22

<210> SEQ ID NO 54
<211> LENGTH: 22
<212> TYPE: DNA
<213> ORGANISM: Artificial Sequence
<220> FEATURE:
<223> OTHER INFORMATION: synthetic primer

<400> SEQUENCE: 54
gcggtttagc aagtttgagg tt                                              22

<210> SEQ ID NO 55
<211> LENGTH: 25
<212> TYPE: DNA
<213> ORGANISM: Artificial Sequence
<220> FEATURE:
<223> OTHER INFORMATION: synthetic primer

<400> SEQUENCE: 55
gatctcgtaa gagggagcta atctg                                           25

<210> SEQ ID NO 56
<211> LENGTH: 23
<212> TYPE: DNA
<213> ORGANISM: Artificial Sequence
<220> FEATURE:
<223> OTHER INFORMATION: synthetic primer

<400> SEQUENCE: 56
gactggccta tcactgacgt tta                                             23

<210> SEQ ID NO 57
<211> LENGTH: 22
<212> TYPE: DNA
<213> ORGANISM: Artificial Sequence
<220> FEATURE:
<223> OTHER INFORMATION: synthetic primer

<400> SEQUENCE: 57
gactggccta tcactgacgt tt                                              22

<210> SEQ ID NO 58
<211> LENGTH: 22
<212> TYPE: DNA
<213> ORGANISM: Artificial Sequence
<220> FEATURE:
<223> OTHER INFORMATION: synthetic primer

<400> SEQUENCE: 58
gaaggcagct aactggacat at                                              22

<210> SEQ ID NO 59
<211> LENGTH: 25
<212> TYPE: DNA
<213> ORGANISM: Artificial Sequence
<220> FEATURE:
<223> OTHER INFORMATION: synthetic primer

<400> SEQUENCE: 59
agttactaac gagtcatgtc gagga                                           25

<210> SEQ ID NO 60
<211> LENGTH: 25
<212> TYPE: DNA
<213> ORGANISM: Artificial Sequence
<220> FEATURE:
<223> OTHER INFORMATION: synthetic primer

```
<400> SEQUENCE: 60
agttactaac gagtcatgtc gagga                                      25

<210> SEQ ID NO 61
<211> LENGTH: 25
<212> TYPE: DNA
<213> ORGANISM: Artificial Sequence
<220> FEATURE:
<223> OTHER INFORMATION: synthetic primer

<400> SEQUENCE: 61
agttactaac gagtcatgtc gagga                                      25

<210> SEQ ID NO 62
<211> LENGTH: 24
<212> TYPE: DNA
<213> ORGANISM: Artificial Sequence
<220> FEATURE:
<223> OTHER INFORMATION: synthetic primer

<400> SEQUENCE: 62
cggtggagca tgtggtttaa tttg                                       24

<210> SEQ ID NO 63
<211> LENGTH: 24
<212> TYPE: DNA
<213> ORGANISM: Artificial Sequence
<220> FEATURE:
<223> OTHER INFORMATION: synthetic primer

<400> SEQUENCE: 63
gctgggtcta tactgacact gatg                                       24

<210> SEQ ID NO 64
<211> LENGTH: 24
<212> TYPE: DNA
<213> ORGANISM: Artificial Sequence
<220> FEATURE:
<223> OTHER INFORMATION: synthetic primer

<400> SEQUENCE: 64
ggcagctaac tgggaacata ttga                                       24

<210> SEQ ID NO 65
<211> LENGTH: 22
<212> TYPE: DNA
<213> ORGANISM: Artificial Sequence
<220> FEATURE:
<223> OTHER INFORMATION: synthetic primer

<400> SEQUENCE: 65
gaaggcagct tactgggtct at                                         22

<210> SEQ ID NO 66
<211> LENGTH: 24
<212> TYPE: DNA
<213> ORGANISM: Artificial Sequence
<220> FEATURE:
<223> OTHER INFORMATION: synthetic primer

<400> SEQUENCE: 66
ggcagctaac tggttatata ttga                                       24

<210> SEQ ID NO 67
```

```
<211> LENGTH: 22
<212> TYPE: DNA
<213> ORGANISM: Artificial Sequence
<220> FEATURE:
<223> OTHER INFORMATION: synthetic primer

<400> SEQUENCE: 67
gaaggcagct aactggacat at                                              22

<210> SEQ ID NO 68
<211> LENGTH: 20
<212> TYPE: DNA
<213> ORGANISM: Artificial Sequence
<220> FEATURE:
<223> OTHER INFORMATION: synthetic primer

<400> SEQUENCE: 68
ctccccacac tttcaactct                                                 20

<210> SEQ ID NO 69
<211> LENGTH: 20
<212> TYPE: DNA
<213> ORGANISM: Artificial Sequence
<220> FEATURE:
<223> OTHER INFORMATION: synthetic primer

<400> SEQUENCE: 69
ctccccacac tttcaatcct                                                 20

<210> SEQ ID NO 70
<211> LENGTH: 25
<212> TYPE: DNA
<213> ORGANISM: Artificial Sequence
<220> FEATURE:
<223> OTHER INFORMATION: synthetic primer

<400> SEQUENCE: 70
gtctatactg acactgatgc acgaa                                           25

<210> SEQ ID NO 71
<211> LENGTH: 25
<212> TYPE: DNA
<213> ORGANISM: Artificial Sequence
<220> FEATURE:
<223> OTHER INFORMATION: synthetic primer

<400> SEQUENCE: 71
tgtggtagag agttctggaa ctcca                                           25

<210> SEQ ID NO 72
<211> LENGTH: 25
<212> TYPE: DNA
<213> ORGANISM: Artificial Sequence
<220> FEATURE:
<223> OTHER INFORMATION: synthetic primer

<400> SEQUENCE: 72
tgtggtaggg agttttggaa tttca                                           25

<210> SEQ ID NO 73
<211> LENGTH: 26
<212> TYPE: DNA
<213> ORGANISM: Artificial Sequence
<220> FEATURE:
<223> OTHER INFORMATION: synthetic primer

<400> SEQUENCE: 73
```
gcccaacact tagttctcat cgttta          26

<210> SEQ ID NO 74
<211> LENGTH: 26
<212> TYPE: DNA
<213> ORGANISM: Artificial Sequence
<220> FEATURE:
<223> OTHER INFORMATION: synthetic primer

<400> SEQUENCE: 74
caacacttag ttctcatcgt ttacgg          26

<210> SEQ ID NO 75
<211> LENGTH: 26
<212> TYPE: DNA
<213> ORGANISM: Artificial Sequence
<220> FEATURE:
<223> OTHER INFORMATION: synthetic primer

<400> SEQUENCE: 75
cccaacactt agttctcatc gtttac          26

<210> SEQ ID NO 76
<211> LENGTH: 23
<212> TYPE: DNA
<213> ORGANISM: Artificial Sequence
<220> FEATURE:
<223> OTHER INFORMATION: synthetic primer

<400> SEQUENCE: 76
tcatcgttta cagcgtggac tac          23

<210> SEQ ID NO 77
<211> LENGTH: 20
<212> TYPE: DNA
<213> ORGANISM: Artificial Sequence
<220> FEATURE:
<223> OTHER INFORMATION: synthetic primer

<400> SEQUENCE: 77
ctccccacac tttcaagcct          20

<210> SEQ ID NO 78
<211> LENGTH: 24
<212> TYPE: DNA
<213> ORGANISM: Artificial Sequence
<220> FEATURE:
<223> OTHER INFORMATION: synthetic primer

<400> SEQUENCE: 78
cctatttgct ccccacactt tcaa          24

<210> SEQ ID NO 79
<211> LENGTH: 29
<212> TYPE: DNA
<213> ORGANISM: Artificial Sequence
<220> FEATURE:
<223> OTHER INFORMATION: synthetic primer

<400> SEQUENCE: 79
gcttacctct cttgcattct agtaataca          29

<210> SEQ ID NO 80
<211> LENGTH: 24
<212> TYPE: DNA

```
<213> ORGANISM: Artificial Sequence
<220> FEATURE:
<223> OTHER INFORMATION: synthetic primer

<400> SEQUENCE: 80
cctatttgct ccccacactt tcaa                                                24

<210> SEQ ID NO 81
<211> LENGTH: 20
<212> TYPE: DNA
<213> ORGANISM: Artificial Sequence
<220> FEATURE:
<223> OTHER INFORMATION: synthetic primer

<400> SEQUENCE: 81
ctccccacac tttcaagcct                                                    20

<210> SEQ ID NO 82
<211> LENGTH: 21
<212> TYPE: DNA
<213> ORGANISM: Artificial Sequence
<220> FEATURE:
<223> OTHER INFORMATION: synthetic primer

<400> SEQUENCE: 82
cgtttacagc gtggactacc a                                                  21

<210> SEQ ID NO 83
<211> LENGTH: 24
<212> TYPE: DNA
<213> ORGANISM: Artificial Sequence
<220> FEATURE:
<223> OTHER INFORMATION: synthetic primer

<400> SEQUENCE: 83
caggcggatc atttaatgcg ttag                                               24

<210> SEQ ID NO 84
<211> LENGTH: 29
<212> TYPE: DNA
<213> ORGANISM: Artificial Sequence
<220> FEATURE:
<223> OTHER INFORMATION: synthetic primer

<400> SEQUENCE: 84
gcttacctct cttgcattct agtaataca                                          29

<210> SEQ ID NO 85
<211> LENGTH: 24
<212> TYPE: DNA
<213> ORGANISM: Artificial Sequence
<220> FEATURE:
<223> OTHER INFORMATION: synthetic primer

<400> SEQUENCE: 85
cgtggactac cagggtatct aatc                                               24

<210> SEQ ID NO 86
<211> LENGTH: 25
<212> TYPE: DNA
<213> ORGANISM: Artificial Sequence
<220> FEATURE:
<223> OTHER INFORMATION: synthetic primer

<400> SEQUENCE: 86
tggactacca gggtatctaa tcctg                                              25
```

<210> SEQ ID NO 87
<211> LENGTH: 20
<212> TYPE: DNA
<213> ORGANISM: Artificial Sequence
<220> FEATURE:
<223> OTHER INFORMATION: synthetic primer

<400> SEQUENCE: 87
ctccccacac tttcaagcct                                          20

<210> SEQ ID NO 88
<211> LENGTH: 21
<212> TYPE: DNA
<213> ORGANISM: Artificial Sequence
<220> FEATURE:
<223> OTHER INFORMATION: synthetic primer

<400> SEQUENCE: 88
cgtttacagc gtggactacc a                                        21

<210> SEQ ID NO 89
<211> LENGTH: 23
<212> TYPE: DNA
<213> ORGANISM: Artificial Sequence
<220> FEATURE:
<223> OTHER INFORMATION: synthetic primer

<400> SEQUENCE: 89
cgctttcgtc ccttagtgtc aat                                      23

<210> SEQ ID NO 90
<211> LENGTH: 23
<212> TYPE: DNA
<213> ORGANISM: Artificial Sequence
<220> FEATURE:
<223> OTHER INFORMATION: synthetic primer

<400> SEQUENCE: 90
cgctttcgtc ccttagtgtc aat                                      23

<210> SEQ ID NO 91
<211> LENGTH: 24
<212> TYPE: DNA
<213> ORGANISM: Artificial Sequence
<220> FEATURE:
<223> OTHER INFORMATION: synthetic primer

<400> SEQUENCE: 91
cctatttgct ccccacactt tcaa                                     24

<210> SEQ ID NO 92
<211> LENGTH: 29
<212> TYPE: DNA
<213> ORGANISM: Artificial Sequence
<220> FEATURE:
<223> OTHER INFORMATION: synthetic primer

<400> SEQUENCE: 92
gcttacctct cttgcattct agtaataca                                29

<210> SEQ ID NO 93
<211> LENGTH: 25
<212> TYPE: DNA
<213> ORGANISM: Artificial Sequence
<220> FEATURE:

<223> OTHER INFORMATION: synthetic primer

<400> SEQUENCE: 93
agtgatccaa acggaccttt taaca                                    25

<210> SEQ ID NO 94
<211> LENGTH: 24
<212> TYPE: DNA
<213> ORGANISM: Artificial Sequence
<220> FEATURE:
<223> OTHER INFORMATION: synthetic primer

<400> SEQUENCE: 94
cgtggactac cagggtatct aatc                                     24

<210> SEQ ID NO 95
<211> LENGTH: 25
<212> TYPE: DNA
<213> ORGANISM: Artificial Sequence
<220> FEATURE:
<223> OTHER INFORMATION: synthetic primer

<400> SEQUENCE: 95
gcaccatctg tcattctgtt aacct                                    25

<210> SEQ ID NO 96
<211> LENGTH: 25
<212> TYPE: DNA
<213> ORGANISM: Artificial Sequence
<220> FEATURE:
<223> OTHER INFORMATION: synthetic primer

<400> SEQUENCE: 96
gcaccacctg tcattgggtt gacct                                    25

<210> SEQ ID NO 97
<211> LENGTH: 25
<212> TYPE: DNA
<213> ORGANISM: Artificial Sequence
<220> FEATURE:
<223> OTHER INFORMATION: synthetic primer

<400> SEQUENCE: 97
gcaccatctg tcaccctgtt aacct                                    25

<210> SEQ ID NO 98
<211> LENGTH: 25
<212> TYPE: DNA
<213> ORGANISM: Artificial Sequence
<220> FEATURE:
<223> OTHER INFORMATION: synthetic primer

<400> SEQUENCE: 98
gcaccatctg tcactccgtt aacct                                    25

<210> SEQ ID NO 99
<211> LENGTH: 30
<212> TYPE: DNA
<213> ORGANISM: Artificial Sequence
<220> FEATURE:
<223> OTHER INFORMATION: synthetic primer

<400> SEQUENCE: 99
gcttgatatc actattttgc ttctctttgt                               30

```
<210> SEQ ID NO 100
<211> LENGTH: 30
<212> TYPE: DNA
<213> ORGANISM: Artificial Sequence
<220> FEATURE:
<223> OTHER INFORMATION: synthetic primer

<400> SEQUENCE: 100
gctccaggtc accctatcgc ttctctttgt                              30

<210> SEQ ID NO 101
<211> LENGTH: 22
<212> TYPE: DNA
<213> ORGANISM: Artificial Sequence
<220> FEATURE:
<223> OTHER INFORMATION: synthetic primer

<400> SEQUENCE: 101
caattactcg ggcagtctcc tt                                      22

<210> SEQ ID NO 102
<211> LENGTH: 24
<212> TYPE: DNA
<213> ORGANISM: Artificial Sequence
<220> FEATURE:
<223> OTHER INFORMATION: synthetic primer

<400> SEQUENCE: 102
tctccgaagt taacaaaccg actt                                    24

<210> SEQ ID NO 103
<211> LENGTH: 24
<212> TYPE: DNA
<213> ORGANISM: Artificial Sequence
<220> FEATURE:
<223> OTHER INFORMATION: synthetic primer

<400> SEQUENCE: 103
tccttgcggt tagaataccg actt                                    24

<210> SEQ ID NO 104
<211> LENGTH: 22
<212> TYPE: DNA
<213> ORGANISM: Artificial Sequence
<220> FEATURE:
<223> OTHER INFORMATION: synthetic primer

<400> SEQUENCE: 104
catattgctt ctctttgtac cg                                      22

<210> SEQ ID NO 105
<211> LENGTH: 22
<212> TYPE: DNA
<213> ORGANISM: Artificial Sequence
<220> FEATURE:
<223> OTHER INFORMATION: synthetic primer

<400> SEQUENCE: 105
cacttcgctt ctctttgtac cg                                      22

<210> SEQ ID NO 106
<211> LENGTH: 22
<212> TYPE: DNA
<213> ORGANISM: Artificial Sequence
<220> FEATURE:
<223> OTHER INFORMATION: synthetic primer
```

```
<400> SEQUENCE: 106
catattgctt ctctttgtac cg                                              22

<210> SEQ ID NO 107
<211> LENGTH: 22
<212> TYPE: DNA
<213> ORGANISM: Artificial Sequence
<220> FEATURE:
<223> OTHER INFORMATION: synthetic primer

<400> SEQUENCE: 107
catattgctt ctctttgtac cg                                              22

<210> SEQ ID NO 108
<211> LENGTH: 22
<212> TYPE: DNA
<213> ORGANISM: Artificial Sequence
<220> FEATURE:
<223> OTHER INFORMATION: synthetic primer

<400> SEQUENCE: 108
catattgctt ctctttgtac cg                                              22

<210> SEQ ID NO 109
<211> LENGTH: 22
<212> TYPE: DNA
<213> ORGANISM: Artificial Sequence
<220> FEATURE:
<223> OTHER INFORMATION: synthetic primer

<400> SEQUENCE: 109
catattgctt ctctttgtac cg                                              22

<210> SEQ ID NO 110
<211> LENGTH: 22
<212> TYPE: DNA
<213> ORGANISM: Artificial Sequence
<220> FEATURE:
<223> OTHER INFORMATION: synthetic primer

<400> SEQUENCE: 110
ggattcgcaa ctgtttgtaa tg                                              22

<210> SEQ ID NO 111
<211> LENGTH: 22
<212> TYPE: DNA
<213> ORGANISM: Artificial Sequence
<220> FEATURE:
<223> OTHER INFORMATION: synthetic primer

<400> SEQUENCE: 111
catattgctt ctctttgtac cg                                              22

<210> SEQ ID NO 112
<211> LENGTH: 22
<212> TYPE: DNA
<213> ORGANISM: Artificial Sequence
<220> FEATURE:
<223> OTHER INFORMATION: synthetic primer

<400> SEQUENCE: 112
cctatcgctt ctctttgttc ca                                              22

<210> SEQ ID NO 113
<211> LENGTH: 25
```

```
<212> TYPE: DNA
<213> ORGANISM: Artificial Sequence
<220> FEATURE:
<223> OTHER INFORMATION: synthetic primer

<400> SEQUENCE: 113
gcaccatctg tcattctgtt aacct                                    25

<210> SEQ ID NO 114
<211> LENGTH: 25
<212> TYPE: DNA
<213> ORGANISM: Artificial Sequence
<220> FEATURE:
<223> OTHER INFORMATION: synthetic primer

<400> SEQUENCE: 114
gcaccacctg tcattgggtt gacct                                    25

<210> SEQ ID NO 115
<211> LENGTH: 25
<212> TYPE: DNA
<213> ORGANISM: Artificial Sequence
<220> FEATURE:
<223> OTHER INFORMATION: synthetic primer

<400> SEQUENCE: 115
gcaccatctg tcaccctgtt aacct                                    25

<210> SEQ ID NO 116
<211> LENGTH: 25
<212> TYPE: DNA
<213> ORGANISM: Artificial Sequence
<220> FEATURE:
<223> OTHER INFORMATION: synthetic primer

<400> SEQUENCE: 116
gcaccatctg tcactccgtt aacct                                    25

<210> SEQ ID NO 117
<211> LENGTH: 24
<212> TYPE: DNA
<213> ORGANISM: Artificial Sequence
<220> FEATURE:
<223> OTHER INFORMATION: synthetic primer

<400> SEQUENCE: 117
tctccgaagt taacaaaccg actt                                     24

<210> SEQ ID NO 118
<211> LENGTH: 24
<212> TYPE: DNA
<213> ORGANISM: Artificial Sequence
<220> FEATURE:
<223> OTHER INFORMATION: synthetic primer

<400> SEQUENCE: 118
tccttgcggt tagaataccg actt                                     24

<210> SEQ ID NO 119
<211> LENGTH: 24
<212> TYPE: DNA
<213> ORGANISM: Artificial Sequence
<220> FEATURE:
<223> OTHER INFORMATION: synthetic primer

<400> SEQUENCE: 119
```
ccccgatctc ttagtgaagc aaac                    24

<210> SEQ ID NO 120
<211> LENGTH: 24
<212> TYPE: DNA
<213> ORGANISM: Artificial Sequence
<220> FEATURE:
<223> OTHER INFORMATION: synthetic primer

<400> SEQUENCE: 120
ccctcatctc ttagcggagc aaac                    24

<210> SEQ ID NO 121
<211> LENGTH: 24
<212> TYPE: DNA
<213> ORGANISM: Artificial Sequence
<220> FEATURE:
<223> OTHER INFORMATION: synthetic primer

<400> SEQUENCE: 121
tccccatctc atagtgaacc aaac                    24

<210> SEQ ID NO 122
<211> LENGTH: 23
<212> TYPE: DNA
<213> ORGANISM: Artificial Sequence
<220> FEATURE:
<223> OTHER INFORMATION: synthetic primer

<400> SEQUENCE: 122
tcatcgttta cggcgtggac tac                     23

<210> SEQ ID NO 123
<211> LENGTH: 24
<212> TYPE: DNA
<213> ORGANISM: Artificial Sequence
<220> FEATURE:
<223> OTHER INFORMATION: synthetic primer

<400> SEQUENCE: 123
cctatttgct ccccacactt tcaa                    24

<210> SEQ ID NO 124
<211> LENGTH: 20
<212> TYPE: DNA
<213> ORGANISM: Artificial Sequence
<220> FEATURE:
<223> OTHER INFORMATION: synthetic primer

<400> SEQUENCE: 124
ctccccacac tttcaagcct                         20

<210> SEQ ID NO 125
<211> LENGTH: 29
<212> TYPE: DNA
<213> ORGANISM: Artificial Sequence
<220> FEATURE:
<223> OTHER INFORMATION: synthetic primer

<400> SEQUENCE: 125
gcttacctct cttgcattct agtaaaaca               29

<210> SEQ ID NO 126
<211> LENGTH: 29
<212> TYPE: DNA
<213> ORGANISM: Artificial Sequence

```
<220> FEATURE:
<223> OTHER INFORMATION: synthetic primer

<400> SEQUENCE: 126
gcttacctct cttgcattct agtaaaaca                                      29

<210> SEQ ID NO 127
<211> LENGTH: 24
<212> TYPE: DNA
<213> ORGANISM: Artificial Sequence
<220> FEATURE:
<223> OTHER INFORMATION: synthetic primer

<400> SEQUENCE: 127
gattactagc gattccggct tcat                                           24

<210> SEQ ID NO 128
<211> LENGTH: 23
<212> TYPE: DNA
<213> ORGANISM: Artificial Sequence
<220> FEATURE:
<223> OTHER INFORMATION: synthetic primer

<400> SEQUENCE: 128
caccgaactt agtccgacac tta                                            23

<210> SEQ ID NO 129
<211> LENGTH: 22
<212> TYPE: DNA
<213> ORGANISM: Artificial Sequence
<220> FEATURE:
<223> OTHER INFORMATION: synthetic primer

<400> SEQUENCE: 129
caccgaactt agtccgacac tt                                             22

<210> SEQ ID NO 130
<211> LENGTH: 25
<212> TYPE: DNA
<213> ORGANISM: Artificial Sequence
<220> FEATURE:
<223> OTHER INFORMATION: synthetic primer

<400> SEQUENCE: 130
tggactacca gggtatctaa tcctg                                          25

<210> SEQ ID NO 131
<211> LENGTH: 25
<212> TYPE: DNA
<213> ORGANISM: Artificial Sequence
<220> FEATURE:
<223> OTHER INFORMATION: synthetic primer

<400> SEQUENCE: 131
ccactcgtaa gaggcatgat gattt                                          25

<210> SEQ ID NO 132
<211> LENGTH: 24
<212> TYPE: DNA
<213> ORGANISM: Artificial Sequence
<220> FEATURE:
<223> OTHER INFORMATION: synthetic primer

<400> SEQUENCE: 132
ccactcgtaa gaggcatgat gatt                                           24
```

<210> SEQ ID NO 133
<211> LENGTH: 26
<212> TYPE: DNA
<213> ORGANISM: Artificial Sequence
<220> FEATURE:
<223> OTHER INFORMATION: synthetic primer

<400> SEQUENCE: 133
cactcgtaag aggcatgatg atttga                                        26

<210> SEQ ID NO 134
<211> LENGTH: 25
<212> TYPE: DNA
<213> ORGANISM: Artificial Sequence
<220> FEATURE:
<223> OTHER INFORMATION: synthetic primer

<400> SEQUENCE: 134
acctccacta tgtctccata gcttt                                         25

<210> SEQ ID NO 135
<211> LENGTH: 24
<212> TYPE: DNA
<213> ORGANISM: Artificial Sequence
<220> FEATURE:
<223> OTHER INFORMATION: synthetic primer

<400> SEQUENCE: 135
gctgggtcta tactgacact gatg                                          24

<210> SEQ ID NO 136
<211> LENGTH: 24
<212> TYPE: DNA
<213> ORGANISM: Artificial Sequence
<220> FEATURE:
<223> OTHER INFORMATION: synthetic primer

<400> SEQUENCE: 136
ggcagctaac tgggaacata ttga                                          24

<210> SEQ ID NO 137
<211> LENGTH: 22
<212> TYPE: DNA
<213> ORGANISM: Artificial Sequence
<220> FEATURE:
<223> OTHER INFORMATION: synthetic primer

<400> SEQUENCE: 137
gaaggcagct tactgggtct at                                            22

<210> SEQ ID NO 138
<211> LENGTH: 24
<212> TYPE: DNA
<213> ORGANISM: Artificial Sequence
<220> FEATURE:
<223> OTHER INFORMATION: synthetic primer

<400> SEQUENCE: 138
ggcagctaac tggttatata ttga                                          24

<210> SEQ ID NO 139
<211> LENGTH: 22
<212> TYPE: DNA
<213> ORGANISM: Artificial Sequence
<220> FEATURE:
<223> OTHER INFORMATION: synthetic primer

```
<400> SEQUENCE: 139
gaaggcagct aactggacat at                                          22

<210> SEQ ID NO 140
<211> LENGTH: 20
<212> TYPE: DNA
<213> ORGANISM: Artificial Sequence
<220> FEATURE:
<223> OTHER INFORMATION: synthetic primer

<400> SEQUENCE: 140
ctccccacac tttcaactct                                             20

<210> SEQ ID NO 141
<211> LENGTH: 20
<212> TYPE: DNA
<213> ORGANISM: Artificial Sequence
<220> FEATURE:
<223> OTHER INFORMATION: synthetic primer

<400> SEQUENCE: 141
ctccccacac tttcaatcct                                             20

<210> SEQ ID NO 142
<211> LENGTH: 21
<212> TYPE: DNA
<213> ORGANISM: Artificial Sequence
<220> FEATURE:
<223> OTHER INFORMATION: synthetic primer

<400> SEQUENCE: 142
cgttaactgc agcactgacc t                                           21

<210> SEQ ID NO 143
<211> LENGTH: 25
<212> TYPE: DNA
<213> ORGANISM: Artificial Sequence
<220> FEATURE:
<223> OTHER INFORMATION: synthetic primer

<400> SEQUENCE: 143
tgtggtagag agttctggaa ctcca                                       25

<210> SEQ ID NO 144
<211> LENGTH: 25
<212> TYPE: DNA
<213> ORGANISM: Artificial Sequence
<220> FEATURE:
<223> OTHER INFORMATION: synthetic primer

<400> SEQUENCE: 144
tgtggtaggg agttttggaa tttca                                       25
```

MULTI-PRIMER ASSAY FOR *MYCOPLASMA* DETECTION

CROSS-REFERENCE TO RELATED APPLICATIONS

This application is a continuation of U.S. application Ser. No. 12/916,420, filed Oct. 29, 2010, which claims the benefit of U.S. Provisional Patent Application No. 61/262,492, filed Nov. 18, 2009, and the benefit of U.S. Provisional Patent Application No. 61/256,413, filed Oct. 30, 2009, the entire disclosure of each of which is incorporated herein by reference.

TECHNICAL FIELD

In general, the present teachings relate to compositions, methods and kits for determining whether contaminating microorganisms are present in a starting material, for example but not limited to a tissue culture sample, a food sample, a water sample, an environmental sample, an agricultural sample, a biopharmaceutical sample, or a pharmaceutical sample.

BACKGROUND

*Mycoplasma* is a common contaminant of cell and tissue culture samples. Infection is persistent, difficult to detect and diagnose, and very difficult to cure. The presence of *Mycoplasma* in infected cultures can change many of the cells' reactions, including altering cell growth rate, inducing morphological changes or cell transformation, and mimicking virus infection. A *Mycoplasma*-contaminated cell line is typically significantly influenced in every respect, and, thus, does not comply with Pharmacopoeia and FDA regulatory requirements. Therefore, there is an absolute requirement for routine, periodic assays for testing of possible contamination of all cell cultures used in manufacturing of pharmaceuticals.

Existing methods for identification of *Mycoplasma* contamination rely on traditional bacterial culturing on agarose plates, taking up to 28 days for results. Such a protracted time between sampling and results preclude efficient quality control (QC) checks, delay production approvals and limit sampling points for QC. PCR-based methods have the greatest potential to become a routine procedure for *Mycoplasma* testing for cell culture, tissue culture, food, environmental, agricultural, biopharmaceutical, and pharmaceutical QC. There remains, however, a need for a *Mycoplasma* detection assay that is, for example, rapid, sensitive, and specific for a variety of *Mycoplasma* species.

SUMMARY

The invention provides, in part, assays, methods and kits for detecting *Mycoplasma* in a sample. In some embodiments, the invention provides a method for a multi-primer assay for detecting *Mycoplasma*, the assay comprising contacting a sample with a plurality of oligonucleotide primers in a single vessel, performing a multi-primer amplification reaction in the single vessel, wherein each of the plurality of oligonucleotide primers is present for participation in amplifying the sample to produce an amplification product, and detecting the amplification product, wherein the presence of an amplification product indicates *Mycoplasma* in the sample. In some embodiments, the plurality of oligonucleotide primers is selected from the group consisting of SEQ ID NOs: 1-144. In some embodiments, at least one of the oligonucleotide primers comprises a modified nucleobase at at least one of the third nucleobase or the second nucleobase from the 3' end of the primer.

In some embodiments, the invention provides a multi-primer assay for detecting *Mycoplasma*, the assay comprising combining a plurality of oligonucleotide primers selected from the group consisting of SEQ ID NOs: 1-144 with a sample to be tested for *Mycoplasma* in a single vessel, contacting the sample with the plurality of oligonucleotide primers in the vessel, performing a multi-primer amplification reaction in the vessel, wherein each of the plurality of oligonucleotide primers is present for participation in amplifying the sample to produce an amplification product, and detecting the amplification product, wherein the presence of an amplification product indicates *Mycoplasma* in the sample.

In some embodiments, the invention provides a method for detecting *Mycoplasma* comprising dispensing in a single vessel a plurality of oligonucleotide primers, introducing a sample to be tested for *Mycoplasma* into contact with the primers in the vessel, performing a multi-primer amplification reaction in the vessel, wherein each of the plurality of oligonucleotide primers is present for participation in amplifying the sample to produce an amplification product, and detecting for the presence of the amplification product, wherein the presence of the amplification product indicates *Mycoplasma* in the sample. In some embodiments, the plurality of oligonucleotide primers is selected from the group consisting of SEQ ID NOs: 1-144.

In some embodiments, provided is a method for detecting *Mycoplasma* comprising extracting nucleic acid from a sample to be tested for *Mycoplasma*, combining in a single vessel a plurality of oligonucleotide primers and the nucleic acid from the sample, contacting the nucleic acid from the sample with the plurality of oligonucleotide primers in the vessel, performing a multi-primer amplification reaction in the vessel, wherein each of the plurality of oligonucleotide primers is present for participation in amplifying the sample to produce an amplification product; and detecting the amplification product, wherein the presence of the amplification product indicates *Mycoplasma* in the sample. In some embodiments, the plurality of oligonucleotide primers is selected from the group consisting of SEQ ID NOs: 1-144.

In some embodiments, the present teachings provide a *Mycoplasma* assay wherein the plurality of oligonucleotide primers present in the multi-primer amplification reaction are at least nine, at least 10, at least 15, at least twenty, at least twenty-five, at least thirty, at least thirty-one, at least thirty-two, at least thirty-three, at least thirty-four, at least thirty-five, at least thirty-six, at least thirty-seven, at least thirty-eight, at least thirty-nine, or at least forty oligonucleotide primers. In some embodiments the amplifying is a polymerase chain reaction (PCR) and the at least some of the oligonucleotide primers are modified nucleobases at the 3' or 2' position from the 3' end of the primer. In some embodiments at least 10 oligonucleotide primer sequences contain a 3' or 2' modified nucleobase from the 3' end of the primer sequence. In some embodiments, the modification to the nucleobase averts primer-dimer formation in the PCR.

In some embodiments, the detection of *Mycoplasma* is in a sample is selected from a cell culture, a tissue culture, a food sample, an environmental sample, an agricultural sample, a biopharmaceutical sample, a pharmaceutical sample, or water.

In some embodiments, the oligonucleotide primer contacts by hybridization to a target nucleic acid in a sample to be tested for *Mycoplasma*. The target nucleic acid may be free in the sample or extracted from the sample prior to contact with the plurality of oligonucleotide primers.

In some embodiments the assay for the detection of *Mycoplasma* and closely related species, strains and substrains utilizes a detector selected from the group consisting of a nucleic acid dye, a reporter probe, or a reporter probe and a nucleic acid dye. In some embodiments, the dye is a SYBR® Green dye.

In some embodiments the assay for the detection of *Mycoplasma* and closely related species, strains and substrains contains a discriminatory positive control (DPC) nucleic acid. The DPC nucleic acid can be added to the sample prior to extraction of the target nucleic acid of the sample or the DPC nucleic acid is extracted simultaneously with the target nucleic acid of the sample. The DPC nucleic acid is amplified in the multi-primer amplification reaction along with the target nucleic acid from the sample, if present. In some embodiments, the DPC amplification product is detected and distinguished from the amplification product of the sample, if present. In some embodiments, the detection of the DPC amplification product and no detection of the *Mycoplasma* amplification product is a confirmed negative assay for *Mycoplasma*. In still other embodiments, the detection of the DPC amplification product and detection of the *Mycoplasma* amplification product is a confirmed positive assay for *Mycoplasma*.

In some embodiments, disclosed is a method for detecting *Mycoplasma* comprising combining a discriminating positive control (DPC) nucleic acid with a sample to be tested for *Mycoplasma*, extracting nucleic acid from the combined sample and DPC, combining in a single vessel a plurality of oligonucleotide primers selected from the group consisting of SEQ ID NOS:1-144 and the extracted nucleic acid, contacting the nucleic acid with the plurality of oligonucleotide primers in the vessel, performing a multi-primer amplification reaction in the vessel, wherein each of the plurality of oligonucleotide primers is present for participation in amplifying the sample to produce an amplification product, and detecting for the presence of the amplification product, wherein detection of the DPC amplification product and detection of the *Mycoplasma* amplification product is a confirmed detection of *Mycoplasma* in the sample.

In some embodiments, the assay for the detection of *Mycoplasma* and related species and subspecies, strains and substrains comprises an amplicon of a discriminatory positive control distinguishable from an amplicon for the *Mycoplasma* and the detecting is by a melting temperature for the discriminatory positive control distinguishable from a melting temperature for the *Mycoplasma* or the detecting comprises a melt curve for the discriminatory positive control distinguishable from a melt curve for the *Mycoplasma*.

In some embodiments, the invention provides assays and methods for detecting *Mycoplasma*, related species and subspecies, and related strains and substrains. In some embodiments, the assay for the detection of *Mycoplasma* and related species and subspecies, strains and substrains detects more than 90 *Mycoplasma* species as well as related microorganisms *Acholeplama laidlwaii* and *Spiroplasma citri*. In some embodiments, the assay detects *Acholeplasma granularum, Acholeplasma pieciae* and numerous *Sprioplasma* species listed in Table 6.

In some embodiments, disclosed is a method of identifying a sample that contains any of the microorganisms listed in Table 6 comprising: PCR amplifying at least one target nucleic acid from the sample that contains any of the microorganisms listed in Table 6 to form at least one target amplicon, wherein the PCR contains a plurality of primers capable of amplifying any of the microorganisms listed in Table 6; and detecting the at least one target amplicon to identify the sample that contains any of the microorganisms listed in Table 6. In some embodiments, the plurality of primers comprises at least 15 forward primers and at least 16 reverse primers selected from the group consisting of SEQ ID NOs:1-144.

In some embodiments, disclosed is a method of reducing false negatives in a PCR querying a sample containing any of the microorganisms listed in Table 6, the method comprising: PCR amplifying at least one target nucleic acid from the sample, wherein the PCR contains a plurality of primers capable of amplifying any of the microorganisms listed in Table 6 to form at least one target amplicon; detecting the at least one target amplicon; and, reducing the false negatives in the PCR as compared to a control PCR querying a sample containing fewer than the plurality of primers. In some embodiments, the plurality of primer pairs comprises at least 15 forward primers and at least 16 reverse primers. In some embodiments, the plurality of primers is selected from the group consisting of SEQ ID NOs:1-144.

In another aspect, the invention is directed to a method of making a primer composition for detection of *Mycoplasma*, related species and subspecies, and related strains and substrains, the method comprising combining a plurality of oligonucleotide primers selected from the group consisting of SEQ ID NOs:1-144.

In some embodiments, disclosed is a multi-primer kit for detecting *Mycoplasma* and related species and subspecies, strains and substrains. The kit comprises a plurality of oligonucleotide primers. The kit can further comprise one or more of a polymerase, a detectable reporter, a protocol and a discriminating positive control. In some embodiments, the detectable reporter is selected from the group consisting of a nucleic acid dye, a reporter probe or a reporter probe and a nucleic acid dye. In some embodiments, the dye is a SYBR® Green dye.

BRIEF DESCRIPTION OF THE DRAWINGS

FIG. 1A is a graph depicting the fluorescence from the PCR amplification cycles and FIG. 1B is a graph depicting the melt curve following amplification.

FIG. 2A is a graph depicting the fluorescence from the PCR amplification cycles and FIG. 2B is a graph depicting the melt curve following amplification.

FIG. 3 is a graph depicting the melt curve of the *Mycoplasma* and DPC amplified DNA.

FIGS. 4A-4F illustrates interpretation of a positive or negative result based on $C_T$ and $T_m$. FIG. 4A is a graph depicting the fluorescence from the PCR amplification cycles of a test sample and FIG. 4B is a graph depicting the following melt curve. FIG. 4C is a graph depicting the fluorescence from the PCR amplification cycles of a second different test sample and FIG. 4D is a graph depicting the following melt curve. FIG. 4E is a graph depicting the fluorescence from the PCR amplification cycles of a third test sample and FIG. 4F is a graph depicting the following melt curve.

DETAILED DESCRIPTION

Figure 1A:
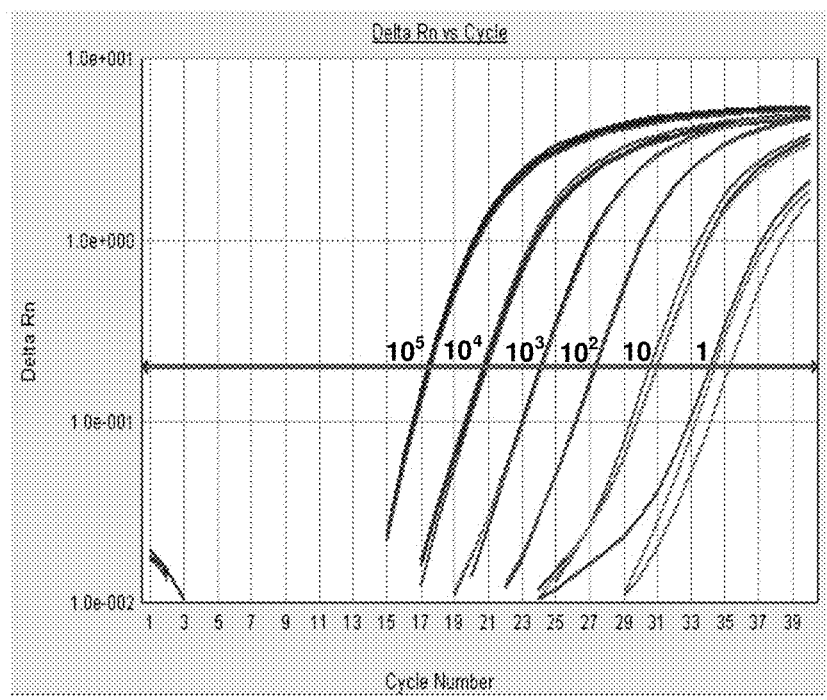
FIGS. 1A-B illustrates the limit of detection (LOD) of a *Mycoplasma* detection assay described herein.

The present invention relates, in part, to real-time PCR assays assays which are rapid and reliable for *Mycoplasma* detection. Applicants have discovered assay components which enable detection of greater than 90 *Mycoplasma* species or strains, while excluding species closely related at the genetic level. As demonstrated herein, the assay can detect 1-10 copies of *Mycoplasma* DNA with high specificity and amplification efficiency close to 100%. Typically, the assay is a closed tube sample analysis method, eliminating post-amplification sample handling and the rapid sample preparation and same-day results allow for in-process testing. In some embodiments, the assay uses a highly optimized Power-SYBR® Green detection technology to provide analysis of multiple parameters for results interpretation.

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. For illustration purposes, but not as a limitation, "X and/or Y" can mean "X" or "Y" or "X and Y". The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of". The term "and/or" means one or all of the listed elements or a combination of any two or more of the listed element.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The practice of the present invention may employ conventional techniques and descriptions of organic chemistry, polymer technology, molecular biology (including recombinant techniques), cell biology, biochemistry, and immunology, which are within the skill of the art. Such conventional techniques include oligonucleotide synthesis, hybridization, extension reaction, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press, 1989), Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2002) Biochemistry, $5^{th}$ Ed., W. H. Freeman Pub., New York, N.Y. all of which are herein incorporated in their entirety by reference for all purposes.

The present teachings provide methods and kits for determining the presence or absence of a given microorganism in a sample, for example but not limited to, a pathogen in a food sample, cultured cells, including but not limited to stem cells, CHO, Vero, HeLa, cultured animal cells, and so on, an agricultural, environmental, or biopharmaceutical sample including but not limited to the research, development, manufacturing and quality control/quality assurance testing of peritoneal, inhalation and topical pharmaceuticals and tissue therapeutics. Microorganisms can include but are not limited to bacteria, virus, *Mycoplasma*, and nucleic acids extracted from the aforementioned samples.

The terms "amplicon," "amplification product" and "amplified sequence" are used interchangeably herein and refer to a broad range of techniques for increasing polynucleotide sequences, either linearly or exponentially and can be the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can comprise thermal-cycling or can be performed isothermally. In various embodiments, the term "amplification product" and "amplified sequence" includes products from any number of cycles of amplification reactions.

The terms "amplifying" and "amplification" are used in a broad sense and refer to any technique by which a target region, an amplicon, or at least part of an amplicon, is reproduced or copied (including the synthesis of a complementary strand), typically in a template-dependent manner, including a broad range of techniques for amplifying nucleic acid sequences, either linearly or exponentially. Some non-limiting examples of amplification techniques include primer extension, including the polymerase chain reaction (PCR), RT-PCR, asynchronous PCR (A-PCR), and asymmetric PCR, strand displacement amplification (SDA), multiple displacement amplification (MDA), nucleic acid strand-based amplification (NASBA), rolling circle amplification (RCA), transcription-mediated amplification (TMA), and the like, including multiplex versions, or combinations thereof. Descriptions of certain amplification techniques can be found in, among other places, Molecular Cloning, A Laboratory Manual, Cold Spring Harbor Press, 3d ed., 2001 (hereinafter "Sambrook and Russell"); Sambrook et al.; Ausubel et al.; PCR Primer: A Laboratory Manual, Diffenbach, Ed., Cold Spring Harbor Press (1995); Msuih et al., J. Clin. Micro. 34:501-07 (1996); McPherson; Rapley; U.S. Pat. Nos. 6,027,998 and 6,511,810; PCT Publication Nos. WO 97/31256 and WO 01/92579; Ehrlich et al., Science 252:1643-50 (1991); Favis et al., Nature Biotechnology 18:561-64 (2000); Protocols & Applications Guide, rev. September 2004, Promega, Madison, Wis.; and Rabenau et al., Infection 28:97-102 (2000).

The terms "annealing" and "hybridizing", including without limitation variations of the root words hybridize and anneal, are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers anneal to complementary or substantially complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349, 1968. In general, whether such annealing takes place is influenced by, among other things, the length of the complementary portion of the primers and their corresponding primer-binding sites in adapter-modified molecules and/or extension products, the pH, the temperature, the presence of mono- and divalent cations, the proportion of G and C nucleotides in the hybridizing region, the viscosity of the medium, and the presence of denaturants. Such variables influence the time required for hybridization. The presence of certain nucleotide analogs or minor groove binders in the complementary portions of the primers and reporter probes can also influence hybridization conditions. Thus, the preferred annealing conditions will depend upon the particular application. Such conditions, however, can be routinely determined by persons of ordinary skill in the art, without undue experimentation. Typically, annealing conditions are selected to allow the disclosed primers to selectively hybridize with a complementary or substantially complementary sequence in their corresponding adapter-modified molecule and/or extension product, but not hybridize to any significant degree to other sequences in the reaction.

As used herein the term "contacting" refers to the hybridization between a primer and its substantially complementary region.

The terms "detecting" and "detection" are used in a broad sense herein and encompass any technique by which one can determine whether or not a particular microorganism, i.e., a microorganism of interest, is present in a sample. In some embodiments, the presence of a surrogate is detected, directly or indirectly, allowing the presence or absence of a microorganism to be determined. For example but not limited to, detecting a family of labeled sequencing products obtained using a microbial amplicon as the template; detecting the fluorescence generated when a nuclease reporter probe, annealed to an amplification product, is cleaved by a polymerase; or detecting the $T_m$ when the fluorescence is no longer detectable due to separation of the strands of the double-stranded amplicon, wherein the detectable signal; detectable change in signal; or differences in $T_m$ indicates that the corresponding microbial target sequence has been amplified and thus the microorganism is present in the sample. In some embodiments, detecting comprises quantitating the detectable signal, including without limitation, a real-time detection method, such as quantitative PCR ("Q-PCR"). In some embodiments, detecting comprises determining the sequence of a sequencing product or a family of sequencing products generated using an amplification product as the template; in some embodiments, such detecting comprises obtaining the sequence of a family of sequencing products.

The term "discriminating positive control" (DPC) as used herein refers to a nucleic acid sequence added to a sample being assayed to access for example, but not limited to, extraction of nucleic acid from the sample, presence of inhibitors precluding nucleic acid detection in the sample, and/or confirm detection of a target nucleic acid sequence in a test sample. The discriminating positive control provides confirmation as seen as a positive result when assaying for the extraction of nucleic acid, the method for the detection of the presence of nucleic acid or the fidelity of the reaction method for the detection of the presence of nucleic acid. The discriminating positive control shares the same primer-binding sites of the microorganism of interest. However, unlike the microorganism of interest, the discriminating positive control can be differentiated from the nucleic acid sequence of the microorganism of interest in that it differs in its nucleic acid sequence, amplicon sequence, melting temperature ($T_m$) and melt curve. Because the positive result for the discriminating positive control is distinguishable from a positive result for the microorganism of interest, the concern of a false positive is removed and provides confidence in the results.

In some embodiments, the discriminating positive control is added prior to extraction of nucleic acid from the test sample which can contain the microorganism of interest to verify the extraction of nucleic acid from the test sample including, if present, extraction of the microorganism of interest as well as the method of extraction. In some embodiments, the discriminating positive control is added to control water, i.e., nucleic acid free water, to serve as a positive control of the reactants for a polymerase chain reaction. In some embodiments, the discriminating positive control is added prior to amplification of the nucleic acid of the microorganism of interest to verify the fidelity of the amplification reaction and rule out inhibitors of the amplification reaction. Inhibitors can be from the extraction reaction or components of the amplification reaction can be inactive, of the wrong concentration, degraded, or inadvertently omitted from the amplification reaction.

As used here, "distinguishing" and "distinguishable" are used interchangeably and refer to differentiating between at least two results from substantially similar or identical reactions, including but not limited to, two different amplification products, two different melting temperatures, two different melt curves, and the like. The results can be from a single reaction, two reactions conducted in parallel, two reactions conducted independently, i.e., separate days, operators, laboratories, and so on.

The term "selectively hybridize" and variations thereof means that, under appropriate stringency conditions, a given sequence (for example but not limited to a primer) anneals with a second sequence comprising a complementary string of nucleotides (for example but not limited to a target flanking sequence or a primer-binding site of an amplicon), but does not anneal to undesired sequences, such as non-target nucleic acids or other primers. Typically, as the reaction temperature increases toward the melting temperature of a particular double-stranded sequence, the relative amount of selective hybridization generally increases and mis-priming generally decreases. In this specification, a statement that one sequence hybridizes or selectively hybridizes with another sequence encompasses situations where the entirety of both of the sequences hybridize to one another, and situations where only a portion of one or both of the sequences hybridizes to the entire other sequence or to a portion of the other sequence.

As used herein, the term "$T_m$" is used in reference to melting temperature. The melting temperature is the temperature at which a population of double-stranded nucleic acid molecules becomes half dissociated into single strands. The $T_m$ can be altered by changes in the length of the molecule and the composition of the nucleotide sequence. For example, a higher $T_m$ can be associated with a high GC content.

As used herein, the term "melt curve" is used in reference to a graphical presentation of an experimental determination of $T_m$. The determination of $T_m$ is well known to one of ordinary skill in the art. For example, the melt curve can be determined following a polymerase chain reaction by heating the population of double-stranded nucleic acid molecules from approximately 60° C. to approximately 90° C. at 0.1 to 1.0 second intervals, and plotting the derivative of the dissociation of the double-stranded nucleic acid verses temperature. The apex of the peak represents the dissociation of half the double-stranded molecules into single strands.

As used herein, the terms "multi-primer" and "multi-primer amplification reaction" refer to at least two or more amplification reactions occurring simultaneously within a single amplification reaction vessel. The multi-primer amplification reaction according to the present teachings provides for simultaneous amplification of a plurality of amplification primers if the target nucleic acid sequence to which each of the primers would hybridize is present in the amplification reaction. For example, in a multi-primer reaction containing twelve primer pairs and two target nucleic acid sequences, then, at least one primer pair for a first target nucleic acid sequence and a second primer pair for a second target sequence would be expected to hybridize to their respective targets and the targets would be expected to be amplified in the subsequent amplification reaction. In the example, the first target nucleic acid can be a discriminating positive control and the second target nucleic acid can be *Mycoplasma* sp.

The term "multi-primer assay" refers to an assay involving a multi-primer amplification reaction.

The term "modified nucleobase" refers to a chemical alteration to a nucleotide.

The term "nucleobase" refers to a nucleotide within a DNA or RNA sequence.

As used herein, "nucleobase numbering" refers to the nucleobase position within an oligonucleotide sequence, e.g., a primer sequence. The first nucleobase can the 5' most nucleobase, the second the one to the right, reading left to right, 5' to 3'. While the second nucleobase from the 3' end refers to the second nucleobase to the left of the last nucleobase in the sequence, reading right to left, 3' to 5'.

As used herein, "presence" refers to the existence (and so the detection) of an amplification product resulting from an amplification reaction.

The term "primer" refers to a polynucleotide and analogs thereof that are capable of selectively hybridizing to a target nucleic acid or "template", a target region flanking sequence or to a corresponding primer-binding site of an amplification product; and allows the synthesis of a sequence complementary to the corresponding polynucleotide template, flanking sequence or amplification product from the primer's 3' end. Typically a primer can be between about 10 to 100 nucleotides in length and can provide a point of initiation for template-directed synthesis of a polynucleotide complementary to the template, which can take place in the presence of appropriate enzyme(s), cofactors, substrates such as nucleotides and the like.

As used herein, the term "amplification primer" refers to an oligonucleotide, capable of annealing to an RNA or DNA region adjacent a target sequence, and serving as an initiation primer for DNA synthesis under suitable conditions well known in the art. Typically, a PCR reaction employs a pair of amplification primers including an "upstream" or "forward" primer and a "downstream" or "reverse" primer, which delimit a region of the RNA or DNA to be amplified.

As used herein, the term "primer-binding site" refers to a region of a polynucleotide sequence, typically a sequence flanking a target region and/or an amplicon that can serve directly, or by virtue of its complement, as the template upon which a primer can anneal for any suitable primer extension reaction known in the art, for example but not limited to, PCR. It will be appreciated by those of skill in the art that when two primer-binding sites are present on a single polynucleotide, the orientation of the two primer-binding sites is generally different. For example, one primer of a primer pair is complementary to and can hybridize with the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. A primer-binding site of an amplicon may, but need not comprise the same sequence as or at least some of the sequence of the target flanking sequence or its complement.

As used herein the term "primer-dimer" refers to a primer annealing to another primer, including copies of the same primer sequence, a reverse direction primer or another, different primer sequence.

Those in the art understand that as a target region and/or an amplification product is amplified by certain amplification means, the complement of the primer-binding site is synthesized in the complementary amplicon or the complementary strand of the amplicon. Thus, it is to be understood that the complement of a primer-binding site is expressly included within the intended meaning of the term primer-binding site, as used herein.

As used herein, the terms "polynucleotide", "oligonucleotide", and "nucleic acid" are used interchangeably and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and can include nucleotide analogs. The nucleotide monomer units may comprise any nucleotide or nucleotide analog. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted.

As used herein, the terms "target polynucleotide," "nucleic acid target" and "target nucleic acid" are used interchangeably herein and refer to a particular nucleic acid sequence of interest. The "target" can be a polynucleotide sequence that is sought to be amplified and can exist in the presence of other nucleic acid molecules or within a larger nucleic acid molecule. The target polynucleotide can be obtained from any source, and can comprise any number of different compositional components. For example, the target can be nucleic acid (e.g. DNA or RNA), ribosomal DNA (rDNA) and transfer RNA, as well as messenger RNA (mRNA) and/or micro RNA (miRNA). The target can be methylated, non-methylated, or both. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in, for example, but not limited to, forensics samples (see for example Butler, 2001, Forensic DNA Typing: Biology and Technology Behind STR Markers). The target polynucleotides of the present teachings can be derived from any of a number of sources. These sources may include, but are not limited to, cell culture, tissue culture, environmental samples (for example, agricultural, water, and soil), research samples generally, purified samples generally, cultured cells, lysed cells, synthetic biologicals including the manufacturing, processing and storage conditions, as well as manufacturing samples, including biopharmaceutical and pharmaceutical manufacturing samples and the resulting biopharmaceutical and pharmaceutical products. These sources may also include, without limitation, viruses, prokaryotes, eukaryotes, for example, but not limited to plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs. In some embodiments, the target polynucleotide is nucleic acid molecule contained within, isolated or extracted from a pathogen in a food sample, cultured cells, including but not limited to stem cells, CHO, Vero, HeLa, cultured animal cells, and so on, an agricultural, environmental, or biopharmaceutical sample including but not limited to the research, development, manufacturing and quality control/quality assurance testing of peritoneal, inhalation and topical pharmaceuticals and tissue therapeutics.

It will be appreciated that target polynucleotides can be isolated from samples using any of a variety of procedures known in the art, for example the PrepSEQ™ Kits (from Applied Biosystems), Boom et al., and U.S. Pat. No. 5,234,809, mirVana RNA isolation kit (Ambion), etc. It will be appreciated that target polynucleotides can be cut or sheared prior to analysis, including the use of such procedures as mechanical force, sonication, restriction endonuclease cleavage, or any method known in the art.

As used herein, the term "reaction vessel" generally refers to any container, chamber, device, or assembly, in which a reaction can occur in accordance with the present teachings. In some embodiments, a reaction vessel can be a microtube, for example but not limited to a 0.2 mL or a 0.5 mL reaction tube such as a MicroAmp® Optical tube (Applied Biosystems) or a micro-centrifuge tube, or other containers of the sort in common practice in molecular biology laboratories. In some embodiments, a reaction vessel comprises a well of a multi-well plate, a spot on a glass slide, or a channel or chamber of a microfluidics device, including without limitation an Applied Biosystems TaqMan Low Density Array. For example but not as a limitation, a plurality of reaction vessels can reside on the same support. In some embodiments, lab-on-a-chip like devices, available for example from Caliper and Fluidigm, can serve as reaction vessels in the disclosed methods. It will be recognized that a variety of reaction vessels are commercially available or can be designed for use in the context of the present teachings.

The terms "reporter group" and "detectable reporter" as used in a broad sense herein and refer to any identifiable or detectable tag, label, or moiety.

The term "culture medium" as used herein refers to a composition, oftentimes a liquid that is suitable for supporting the growth of a microorganism of interest. A culture medium can be a general- or all-purpose medium, capable of supporting the growth of a variety of different microorganisms. In certain embodiments, the culture media comprises a selective media or an enrichment media. A selective media comprises at least one component that prevents or retards the growth of unwanted microorganisms without inhibiting the growth of the microorganism(s) of interest, for example but not limited to certain dyes, antimicrobials, or salts. An enrichment media comprises at least one component that enhances the growth of the microorganism(s) of interest and it may or may not be designed to inhibit the growth of other microorganisms. Those in the art will appreciate a particular culture media may be selective or inhibitory for the growth of a given microorganism, but that suitable culture media can be identified by consulting the scientific literature or can be determined by routine experimentation. Non-limiting examples of culture media include Brain Heart Infusion (BHI) broth, Fraser broth, and tryptic soy broth. In some embodiments, a culture medium can be solid or semi-solid and can, but need not, include agar.

The term "microorganism" is used in a broad sense herein and includes cells, tissues and organs from plants and animals, including but not limited to, stem cells, CHO, Vero, Hela, cultured animal cells, and so on, genetically modified plants, non-cellular and unicellular organisms, such as eubacteria, including without limitation cyanobacteria; archaea; protozoa; fungi, including but not limited to, algae and yeast; and certain viruses.

Some non-limiting examples of microorganisms include yeast, *Mycoplasma, Escherichia coli*, for example but not limited to enterovirulent strains (such as ETEC, EPEC, O157:H7 or EHEC, and EIEC); *Staphylococcus* species, including but not limited to *S. aureus; Streptococcus* species; *Campylobacter* species, including without limitation *C. jejuni* and *C. coli; Salmonella* species, including without limitation *S. enterica; Vibrio* species, including but not limited to *V. cholerae, V. parahaemolyticus*, and *V. vulnificans; Shigella* species, *Giardia lamblia, Cryptosporidium* species including but not limited to *C. parvum* and *C. muris; Bacillus* species, including but not limited to *B. anthracis* and *B. cereus; Brucella* species; *Yersinia* species including without limitation, *Y. enterocolitica, Y. pseudotuberculosis* and *Y. pestis; Aeromonas* species including without limitation *A. hydrophila; Plesiomonas shigelloides; Entamoeba histolytica; Clostridium botulinum; Listeria* species, including without limitation *L. monocytogenes; Anisakis* species and related worms; *Ascaris lumbricoides; Trichuris trichiura*; and viruses, including without limitation rotavirus, Norwalk virus, hepatitis E virus, and hepatitis C virus.

In certain embodiments, the microorganisms to be detected are present in a food sample being evaluated, such as meat, fish, fruit, vegetables, beer, wine, eggs, or milk; and including processed forms of any of these, for example but not limited to: processed meats, for example but not limited to, ground meat, luncheon meat, sausages, and canned meat products; fruit or vegetable juice, jam, jelly, or preserves;

canned fruits and vegetables; egg products, including without limitation dehydrated eggs; and dairy products such as cheese, cottage cheese, butter, sour cream, and cheese curd. Typically a portion of food or beverage is combined with an appropriate liquid, including without limitation water, a buffer solution, or a culture medium, including without limitation, a selective medium or an enrichment medium. In some embodiments, the food is chopped, macerated, liquefied, diced, or homogenized. In some embodiments, large volumes of sample, for example but not limited to, volumes of 100 mL, 250 mL, or more are processed according to the disclosed methods to determine whether a particular microorganism is present in the starting material. According to certain embodiments, a portion of the food or beverage and appropriate liquid are typically combined to form a dilute suspension, for example but not limited to, ratios of about 1:5, 1:10, or 1:20 (w/vol). In some embodiments, a detergent, an emulsifying agent, or both, is added to enhance the solubility of high lipid foods, for example but not limited to butter and certain other dairy products. Those in the art will appreciate that the choice of liquid used to suspend the food or beverage will depend, at least in part, on the starting material (i.e., the food or beverage) and the microorganism(s) of interest; and that the food/beverage to liquid ratio can vary widely, provided that the suspension is sufficiently fluid to process, for example but not limited to, passing it through a filtration media. In certain embodiments, 25 grams of a solid or semi-solid food is combined with 225 mL of a suitable culture media. In some embodiments, 25 mL of a beverage or a liquefied or partially liquefied food is combined with 225 mL of a suitable culture media.

In certain embodiments, the microorganisms to be detected are present in pharmaceutical products, personal care products, dairy products or in samples of plant, animal, human or environmental origin. Microorganisms may also be detected, if present in raw materials, equipment, products or processes used to manufacture or store food, beverages, water, pharmaceutical products, personal care products dairy products or environmental samples, in clinical specimens, equipment, fixtures or products used to treat humans or animals as well as in clinical samples and clinical environments.

Those of skill in the art will appreciate that detection of microorganism contamination is a concern for both food and health safety. Further, the retesting or destruction of contaminated materials such as food, beverages, water, agricultural products, environmental areas and biopharmaceutical and pharmaceutical products involves major financial losses for the producer or manufacturer. Applications of microbial detection include diagnostic research, biopharmaceutical development, genetic analysis, and environmental testing. Users in these areas would benefit from a discriminatory positive control that would provide the user with confirmation of nucleic acid extraction from the test sample, confirmation of the integrity of the positive control and as an inhibition control to monitor the fidelity of the final, post-extraction sample in the amplification reaction and detection process. Users in these areas must be assured of reproducibility from sample-to-sample, run-to-run, lab-to-lab, and instrument-to-instrument. Traditional methods for detecting food pathogens and microbial contaminants can be very tedious, and may include time-consuming enrichment steps in selective growth media (e.g. 12-36 hours or more), thus it often takes several days before results are obtained. Because of the highly infectious nature of certain microorganisms, the seriousness of the resulting diseases and the limited shelf-life and perishability issues with certain foodstuffs, among other things, there is a continuing need for methods and devices to expedite microbial concentration and detection. There is also a need for methods and kits to rapidly detect microorganisms of interest in environmental samples, including without limitation, samples obtained from a potential bioterror environment. There is also a need for methods and kits to rapidly detect microbial contaminants rapidly and conclusively when performing quality control and quality assurance assays during biopharmaceutical and pharmaceutical manufacturing. There is a need for the assessment and verification of nucleic acid recovery and confidence in a negative sample result during the assessment of pharmaceutical manufacturing steps.

The terms "nucleic acid" and "nucleic acid sequence" as used herein, refer to a polymer of ribonucleosides or deoxyribonucleosides that are covalently bonded, typically by phosphodiester linkages between nucleotide subunits. Non-limiting examples of nucleic acids include genomic DNA (gDNA); hnRNA; mRNA; noncoding RNA (ncRNA), including but not limited to rRNA, tRNA, miRNA (micro RNA), siRNA (small interfering RNA), snoRNA (small nucleolar RNA), snRNA (small nuclear RNA) and stRNA (small temporal RNA); fragmented nucleic acid; nucleic acid obtained from subcellular organelles such as mitochondria or chloroplasts; and amplification products comprising nucleotides. Nucleic acids may be naturally-occurring or they may be synthetic. Discussions of nucleic acids may be found in, among other places, Current Protocols in Nucleic Acid Chemistry, S. Beaucage, D. Bergstrom, G. Glick, and R. Jones, eds., John Wiley & Sons, including updates through September 2005 (hereinafter "Beaucage et al."); S. Verma and F. Eckstein, Ann Rev. Biochem., 67:99-134 (1998); S. Buckingham, Horizon Symposia, Understanding the RNAissance, Nature Publishing Group, May 2003 at pages 1-3; S. Eddy, Nature Rev. Genetics 2:919-29 (2001); and Nucleic Acids in Chemistry and Biology, 2d ed., G. Blackburn and M. Gait, eds., Oxford University Press (1996; hereinafter "Blackburn and Gait").

As used herein, the terms "target polynucleotide" and "target nucleic acid" refer to a polynucleotide sequence that is sought to be amplified. In general, the target polynucleotides of the present teachings will be single stranded, though in some embodiments the target polynucleotide can be double stranded, and a single strand can result from denaturation.

The term "nucleic acid dye" or "intercalating dye" as used herein refers to a fluorescent molecule that is specific for a double-stranded polynucleotide or that at least shows a substantially greater fluorescent enhancement when associated with a double-stranded polynucleotide than with a single-stranded polynucleotide. Typically nucleic acid dye molecules associate with double-stranded segments of polynucleotides by intercalating between the base pairs of the double-stranded segment, by binding in the major or minor grooves of the double-stranded segment, or both. Non-limiting examples of nucleic acid dyes include ethidium bromide, DAPI, Hoechst derivatives including without limitation Hoechst 33258 and Hoechst 33342, intercalators comprising a lanthanide chelate (for example but not limited to a nalthalene diimide derivative carrying two fluorescent tetradentate β-diketone-Eu3+ chelates (NDI-(BHHCT-$Eu^{3+}$)$_2$), see, e.g., Nojima et al., Nucl. Acids Res. Supplement No. 1, 105-06 (2001)), ethidium bromide, and certain unsymmetrical cyanine dyes such as SYBR® Green, PicoGreen®, and BOXTO.

An "unsymmetrical cyanine dye", sometimes described in the art as an asymmetric cyanine dye or an asymmetrical cyanine dye, refers to a dye molecule with the general formula $R_2N[CH=CH]_nCH=NR_2$, where n is a small number and the R groups typically comprise at least one benzazole group and at least one quinoline group or at least one pyridine group. Non-limiting examples of unsymmetrical cyanine dyes include [2-[N-(3-dimethylaminopropyl)-N-propylamino]-4-[2,3-dihydro-3-methyl-(benzo-1,3-thiazol-2-yl)-methylidene]-1-phenyl-quinolinium] (SYBR® Green), [2-[N-bis-(3-dimethylaminopropyl)-amino)-amino] 1-4-[2,3-dihydro-3-methyl-(benzo-1,3-thiazol-2-yl)-methylidene]-1-phenyl-quinolinium] (PicoGreen®), 4-[(3-methyl-6-(benzothiazol-2-yl)-2,3-dihydro-(benzo-1,3-thiazole)-2-methylidenefl-1-methyl-pyridinium iodide (BEBO), BOXTO, and BETO. Descriptions of unsymettrical cyanine dyes can be found in, among other places, Karlsson et al., Nucl. Acids Res. 31:6227-34 (2003); Zipper et al., Nucl. Acids Res. 32:e103 (2004); Bengtsson et al., Nucl. Acids Res. 31:e45 (2003); and Goransson et al., Asymmettric cyanine dyes, DNA-Technology 2005, Chalmers University Technology (2005).

The term "reporter probe" refers to a sequence of nucleotides, nucleotide analogs, or nucleotides and nucleotide analogs, that specifically anneals with a corresponding amplicon, for example but not limited to a PCR product, and when detected, including but not limited to a change in intensity or of emitted wavelength, is used to identify and/or quantify the corresponding amplicon or target polynucleotide. Thus, by indirectly detecting the amplicon, one can determine that the corresponding microorganism is present in the sample. Most reporter probes can be categorized based on their mode of action, for example but not limited to: nuclease probes, including without limitation TaqMan® probes; extension probes including without limitation scorpion primers, Lux™ primers, Amplifluors, and the like; and hybridization probes including without limitation molecular beacons, Eclipse probes, light-up probes, pairs of singly-labeled reporter probes, hybridization probe pairs, and the like. In certain embodiments, reporter probes comprise an amide bond, an LNA, a universal base, or combinations thereof, and include stem-loop and stem-less reporter probe configurations. Certain reporter probes are singly-labeled, while other reporter probes are doubly-labeled. Dual probe systems that comprise FRET between adjacently hybridized probes are within the intended scope of the term reporter probe. In certain embodiments, a reporter probe comprises a fluorescent reporter group and a quencher (including without limitation dark quenchers and fluorescent quenchers). Some non-limiting examples of reporter probes include TaqMan® probes; Scorpion probes (also referred to as scorpion primers); Lux™ primers; FRET primers; Eclipse probes; molecular beacons, including but not limited to FRET-based molecular beacons, multicolor molecular beacons, aptamer beacons, PNA beacons, and antibody beacons; labeled PNA clamps, labeled PNA openers, labeled LNA probes, and probes comprising nanocrystals, metallic nanoparticles and similar hybrid probes (see, e.g., Dubertret et al., Nature Biotech. 19:365-70, 2001; Zelphati et al., BioTechniques 28:304-15, 2000). In certain embodiments, reporter probes further comprise minor groove binders including but not limited to TaqMan®MGB probes and TaqMan®MGB-NFQ probes (both from Applied Biosystems). In certain embodiments, reporter probe detection comprises fluorescence polarization detection (see, e.g., Simeonov and Nikiforov, Nucl. Acids Res. 30:e91, 2002).

The term "DNA polymerase" is used in a broad sense herein and refers to any polypeptide that is able to catalyze the addition of deoxyribonucleotides or analogs of deoxyribonucleotides to a nucleic acid polymer in a template dependent manner. For example but not limited to, the sequential addition of deoxyribonucleotides to the 3'-end of a primer that is annealed to a nucleic acid template during a primer extension reaction. Typically DNA polymerases include DNA-dependent DNA polymerases and RNA-dependent DNA polymerases, including reverse transcriptases. Certain reverse transcriptases possess DNA-dependent DNA polymerase activity under certain reaction conditions, including AMV reverse transcriptase and MMLV reverse transcriptase. Such reverse transcriptases with DNA-dependent DNA polymerase activity may be suitable for use with the disclosed methods and are expressly within the contemplation of the current teachings. Descriptions of DNA polymerases can be found in, among other places, Lehninger Principles of Biochemistry, 3d ed., Nelson and Cox, Worth Publishing, New York, N.Y., 2000, particularly Chapters 26 and 29; Twyman, Advanced Molecular Biology: A Concise Reference, Bios Scientific Publishers, New York, N.Y., 1999; Ausubel et al., Current Protocols in Molecular Biology, John Wiley & Sons, Inc., including supplements through May 2005 (hereinafter "Ausubel et al."); Lin and Jaysena, J. Mol. Biol. 271:100-11, 1997; Pavlov et al., Trends in Biotechnol. 22:253-60, 2004; and Enzymatic Resource Guide: Polymerases, 1998, Promega, Madison, Wis. Expressly within the intended scope of the term DNA polymerase are enzymatically active mutants or variants thereof, including enzymes modified to confer different temperature-sensitive properties (see, e.g., U.S. Pat. Nos. 5,773,258; 5,677,152; and 6,183,998; and DNA Amplification: Current Techniques and Applications, Demidov and Broude, eds., Horizon Bioscience, 2004, particularly in Chapter 1.1).

The term "RNA polymerase" is used in a broad sense herein and refers to any polypeptide that is able to catalyze the addition of ribonucleotides or analogs of ribonucleotides to a nucleic acid polymer in a template dependent manner. The RNA polymerase may be, for example, a T bacteriophage RNA polymerase or an SP6 RNA polymerase.

In some embodiments, a primer comprises a "promoter sequence", including without limitation a sequence suitable for binding a T3 RNA polymerase, T7 RNA polymerase, or SP6 RNA polymerase. In some embodiments, a promoter sequence comprises a multiplicity of different sequences suitable for binding an RNA polymerase, for example but not limited to a first sequence suitable for binding a first RNA polymerase and a second sequence suitable for binding a second RNA polymerase. Those in the art understand that as an amplification product is amplified by certain amplification means, the complement of the promoter sequence is synthesized in the complementary amplicon. Thus, it is to be understood that the complement of a promoter sequence is expressly included within the intended meaning of the term promoter sequence, as used herein.

As used herein, "forward" and "reverse" are used to indicate relative orientation of primers on a polynucleotide sequence. For illustration purposes but not as a limitation, consider a single-stranded polynucleotide drawn in a horizontal, left to right orientation with its 5'-end on the left. The "reverse" primer is designed to anneal with the downstream primer-binding site at or near the "3'-end" of this illustrative polynucleotide in a 5' to 3' orientation, right to left. The corresponding "forward primer is designed to anneal with the complement of the upstream primer-binding site at or near the "5'-end" of the polynucleotide in a 5' to 3' "forward" orientation, left to right. Thus, the reverse primer comprises a sequence that is complementary to the reverse or downstream primer-binding site of the polynucleotide and the forward primer comprises a sequence that is the same as the forward or upstream primer-binding site. It is to be understood that the terms "3-end" and "5'-end" as used in this paragraph are illustrative only and do not necessarily refer literally to the respective ends of the polynucleotide. Rather, the only limitation is that the reverse primer of this exemplary primer pair anneals with a reverse primer-binding site that is downstream or to the right of the forward primer-binding site that comprises the same sequence as the corresponding forward primer. As will be recognized by those of skill in the art, these terms are not intended to be limiting, but rather to provide illustrative orientation in a given embodiment.

Multi-element interacting detectors are also within the intended scope of the term detector, such as fluorophore-quencher pairs, including without limitation fluorescent quenchers and dark quenchers (also known as non-fluorescent quenchers). A fluorescent quencher can absorb the fluorescent signal emitted from a fluorophore and after absorbing enough fluorescent energy, the fluorescent quencher can emit fluorescence at a characteristic wavelength, e.g., fluorescent resonance energy transfer (FRET). For example without limitation, the FAM-TAMRA pair can be illuminated at 492 nm, the excitation peak for FAM, and emit fluorescence at 580 nm, the emission peak for TAMRA. A dark quencher, appropriately paired with a fluorescent reporter group, absorbs the fluorescent energy from the fluorophore, but does not itself fluoresce. Rather, the dark quencher dissipates the absorbed energy, typically as heat. Some non-limiting examples of dark or nonfluorescent quenchers include Dabcyl, Black Hole Quenchers, Iowa Black, QSY-7, AbsoluteQuencher, Eclipse non-fluorescent quencher, metal clusters such as gold nanoparticles, and the like. Certain dual-labeled probes comprising fluorophore-quencher pairs can emit fluorescence when the members of the pair are physically separated, for example but without limitation, nuclease probes such as TaqMan® probes. Other dual-labeled probes comprising fluorophore-quencher pairs can emit fluorescence when the members of the pair are spatially separated, for example but not limited to hybridization probes such as molecular beacons or extension probes such as Scorpion primers. Fluorophore-quencher pairs are well known in the art and used extensively for a variety of probes (see, e.g., Yeung et al., BioTechniques 36:266-75, 2004; Dubertret et al., Nat. Biotech. 19:365-70, 2001; and Tyagi et al., Nat. Biotech. 18:1191-96, 2000).

Also herein, the recitations of numerical ranges by endpoints include all numbers subsumed within that range (e.g., 1 to 5 includes 1, 1.5, 2, 2.75, 3, 3.80, 4, 5, etc.).

Various embodiments of the present teachings relate to a multi-primer assay for detecting Mycoplasma in a sample. In some embodiments, the multi-primer assay for detecting Mycoplasma in a sample has a plurality of oligonucleotide primers which are combined in a reaction vessel with a sample and an amplification reaction is performed. In some embodiments an amplification product results from the amplification reaction and the detection of the amplification product indicates Mycoplasma in the sample.

Various multi-primer assays are known to one of skill in the art for the detection of multiple samples simultaneously. Such assays employ, for example, in a polymerase chain reaction (PCR), one or two oligonucleotide primer pairs. Additional sets of primers often result in spurious, artificial amplification products due to the phenomenon of primer dimer formation. Primer dimer results from the 3' portion of a first oligonucleotide primer hybridizing to a second oligonucleotide primer and then, during the amplification reaction, the first primer amplifies the sequence of the second primer rather than the target nucleic acid sequence, which depletes primers available for hybridization to target nucleic acid sequences, as well as enzyme and dNTPs. The result is a poor yield of amplification product and a waste of reaction components. Consequently, multi-priming with a plurality of primer pairs would be counter-intuitive to one of skill in the art.

In some embodiments, the plurality of oligonucleotide primers were designed with the objectives of having specificity for the 16S ribosomal RNA region of Mycoplasma genomes and to be able to detect many of the important Mycoplasma and closely related species as required by the European Pharmcopedia. Each primer was designed using publically disclosed 16S sequences available in databases known to one of skill in the art, e.g., GenBank, available from the National Center for Biotechnology, National Library of Medicine, at The National Institutes of Health, Bethesda, Md., U.S.A. The disclosed primers were thoroughly analyzed in conjunction with these criteria utilizing both laboratory and bioinformative tools. As shown in Table 1, 144 oligonucleotide primers were evaluated.

TABLE 1

| SEQ ID NO | Forward Primer | SEQ ID NO: | Reverse Primer |
|---|---|---|---|
| 1 | GCTGGGTCTATACTGACACTGATG | 73 | GCCCAACACTTAGTTCTCATCGTTTA |
| 2 | GCTTGCTGGGTCTATACTGACA | 74 | CAACACTTAGTTCTCATCGTTTACGG |
| 3 | GCTTGCTGGGTCTATACTGACA | 75 | CCCAACACTTAGTTCTCATCGTTTAC |
| 4 | GGCAGCTAACTGGGAACATATTGA | 76 | TCATCGTTTACAGCGTGGACTAC |
| 5 | GGCGAAAACTTAGGCCATTACTGA | 77 | CTCCCCACACTTTCAAGCCT |
| 6 | GGTAGAGAGTCCTGGAACTCCAT | 78 | CCTATTTGCTCCCCACACTTTCAA |
| 7 | GGTTAAAGTCCGGAGCTCAACT | 79 | GCTTACCTCTCTTGCATTCTAGTAATACA |
| 8 | GTAGAGAGTCCTGGAACTCCATGT | 80 | CCTATTTGCTCCCCACACTTTCAA |
| 9 | TGTGGTAGGGAGTTTTGGAATTTCA | 81 | CTCCCCACACTTTCAAGCCT |
| 10 | CAGCTAACTGGGAACATATTGACACT | 82 | CGTTTACAGCGTGGACTACCA |

TABLE 1-continued

| SEQ ID NO | Forward Primer | SEQ ID NO: | Reverse Primer |
|---|---|---|---|
| 11 | CGAAGGCAGCTTACTGGGT | 83 | CAGGCGGATCATTTAATGCGTTAG |
| 12 | CGGTTTTGCAAGTTTGAGGTTAAAG | 84 | GCTTACCTCTCTTGCATTCTAGTAATACA |
| 13 | GAAGGCAGCTTACTGGGTCTAT | 85 | CGTGGACTACCAGGGTATCTAATC |
| 14 | GAAGGCAGCTTACTGGGTCTAT | 86 | TGGACTACCAGGGTATCTAATCCTG |
| 15 | GAAGGCGAAAACTTAGGCCATTAC | 87 | CTCCCCACACTTTCAAGCCT |
| 16 | GCAGCTAACTGGGAACATATTGACA | 88 | CGTTTACAGCGTGGACTACCA |
| 17 | GCGAAGGCAGCTAACTGGTT | 89 | CGCTTTCGTCCCTTAGTGTCAAT |
| 18 | GCGAAGGCAGCTAACTGGTTATA | 90 | CGCTTTCGTCCCTTAGTGTCAAT |
| 19 | GCGAAGGCGAGGACTTGG | 91 | CCTATTTGCTCCCCACACTTTCAA |
| 20 | GCGGTTTTGCAAGTTTGAGGTT | 92 | GCTTACCTCTCTTGCATTCTAGTAATACA |
| 21 | GAACGGGTGAGTAACACGTATCTAA | 93 | AGTGATCCAAACGGACCTTTTAACA |
| 22 | GAAGGCAGCTAACTGGTTATAT | 94 | CGTGGACTACCAGGGTATCTAATC |
| 23 | GTGGAGCATGTGGTTTAATTTGAAGA | 95 | GCACCATCTGTCATTCTGTTAACCT |
| 24 | GTGGAGCATGTTGCTTAATTCGACGG | 96 | GCACCACCTGTCATTGGGTTGACCT |
| 25 | GTGGAGCATGTGGTTTAATTTGAAGA | 97 | GCACCATCTGTCACCCTGTTAACCT |
| 26 | GTGGAGCATGTGGTTTAATTTGAAGA | 98 | GCACCATCTGTCACTCCGTTAACCT |
| 27 | CGCAACCCTTGTCCTTAGTTACTTT | 99 | GCTTGATATCACTATTTGCTTCTCTTTGT |
| 28 | CGCAACCCTTATTGCTAGTTACCAT | 100 | GCTCCAGGTCACCCTATCGCTTCTCTTTGT |
| 29 | GCAGCTAACTGGGAACATATTGAC | 101 | CAATTACTCGGGCAGTCTCCTT |
| 30 | CGCAACCCTTGTCCTTAGTTACTTTATC | 102 | TCTCCGAAGTTAACAAACCGACTT |
| 31 | CGCAACCCTTGCCGTTAGTTACTCCATT | 103 | TCCTTGCGGTTAGAATACCGACTT |
| 32 | GACAGATGGTGCATGGTT | 104 | CATATTGCTTCTCTTTGTACCG |
| 33 | GACAGATGGTGCATGGTT | 105 | CACTTCGCTTCTCTTTGTACCG |
| 34 | GACAGATGGTGCATGGTTA | 106 | CATATTGCTTCTCTTTGTACCG |
| 35 | GACAGATGGTGCATGGTTT | 107 | CATATTGCTTCTCTTTGTACCG |
| 36 | GACAGATGGTGCATGGTTC | 108 | CATATTGCTTCTCTTTGTACCG |
| 37 | GACAGATGGTGCATGGTTG | 109 | CATATTGCTTCTCTTTGTACCG |
| 38 | GACAGGTGGTGCATGGTT | 110 | GGATTCGCAACTGTTTGTAATG |
| 39 | GACAGGTGGTGCATGGTT | 111 | CATATTGCTTCTCTTTGTACCG |
| 40 | TACAGGTGGTGCACGGTT | 112 | CCTATCGCTTCTCTTTGTTCCA |
| 41 | AGATACGCGTAGAACCTTACCCA | 113 | GCACCATCTGTCATTCTGTTAACCT |
| 42 | CGGTACACGAAAAACCTTACCTA | 114 | GCACCACCTGTCATTGGGTTGACCT |
| 43 | AGATACGCGGAGAACCTTACCCA | 115 | GCACCATCTGTCACCCTGTTAACCT |
| 44 | AGATACGCGGAGAACCTTACCCA | 116 | GCACCATCTGTCACTCCGTTAACCT |
| 45 | CGCAACCCTTGTCCTTAGTTACTTT | 117 | TCTCCGAAGTTAACAAACCGACTT |
| 46 | CGCAACCCTTGCCGTTAGTTACTCC | 118 | TCCTTGCGGTTAGAATACCGACTT |
| 47 | CGAATGGGTGAGTAACACGTACTT | 119 | CCCCGATCTCTTAGTGAAGCAAAC |
| 48 | CGAATGGGTGAGTAACACGTGCTT | 120 | CCCTCATCTCTTAGCGGAGCAAAC |
| 49 | CGAACGGGTGAGTAACACGTATCT | 121 | TCCCCATCTCATAGTGAACCAAAC |

TABLE 1-continued

| SEQ ID NO | Forward Primer | SEQ ID NO: | Reverse Primer |
|---|---|---|---|
| 50 | GGCAGCTAACTGGTTATATATTGA | 122 | TCATCGTTTACGGCGTGGACTAC |
| 51 | GTAGAGAGTTCTGGAACTCCATGT | 123 | CCTATTTGCTCCCCACACTTTCAA |
| 52 | TGTGGTAGAGAGTTCTGGAACTCCA | 124 | CTCCCCACACTTTCAAGCCT |
| 53 | GCGGTTTTGCAAGTTTGAGGTT | 125 | GCTTACCTCTCTTGCATTCTAGTAAAACA |
| 54 | GCGGTTTAGCAAGTTTGAGGTT | 126 | GCTTACCTCTCTTGCATTCTAGTAAAACA |
| 55 | GATCTCGTAAGAGGGAGCTAATCTG | 127 | GATTACTAGCGATTCCGGCTTCAT |
| 56 | GACTGGCCTATCACTGACGTTTA | 128 | CACCGAACTTAGTCCGACACTTA |
| 57 | GACTGGCCTATCACTGACGTTT | 129 | CACCGAACTTAGTCCGACACTT |
| 58 | GAAGGCAGCTAACTGGACATAT | 130 | TGGACTACCAGGGTATCTAATCCTG |
| 59 | AGTTACTAACGAGTCATGTCGAGGA | 131 | CCACTCGTAAGAGGCATGATGATTT |
| 60 | AGTTACTAACGAGTCATGTCGAGGA | 132 | CCACTCGTAAGAGGCATGATGATT |
| 61 | AGTTACTAACGAGTCATGTCGAGGA | 133 | CACTCGTAAGAGGCATGATGATTTGA |
| 62 | CGGTGGAGCATGTGGTTTAATTTG | 134 | ACCTCCACTATGTCTCCATAGCTTT |
| 63 | GCTGGGTCTATACTGACACTGATG | 135 | GCTGGGTCTATACTGACACTGATG |
| 64 | GGCAGCTAACTGGGAACATATTGA | 136 | GGCAGCTAACTGGGAACATATTGA |
| 65 | GAAGGCAGCTTACTGGGTCTAT | 137 | GAAGGCAGCTTACTGGGTCTAT |
| 66 | GGCAGCTAACTGGTTATATATTGA | 138 | GGCAGCTAACTGGTTATATATTGA |
| 67 | GAAGGCAGCTAACTGGACATAT | 139 | GAAGGCAGCTAACTGGACATAT |
| 68 | CTCCCCACACTTTCAACTCT | 140 | CTCCCCACACTTTCAACTCT |
| 69 | CTCCCCACACTTTCAATCCT | 141 | CTCCCCACACTTTCAATCCT |
| 70 | GTCTATACTGACACTGATGCACGAA | 142 | CGTTAACTGCAGCACTGACCT |
| 71 | TGTGGTAGAGAGTTCTGGAACTCCA | 143 | TGTGGTAGAGAGTTCTGGAACTCCA |
| 72 | TGTGGTAGGGAGTTTTGGAATTTCA | 144 | TGTGGTAGGGAGTTTTGGAATTTCA |

Bioinformatic and actual PCR conditions indicated that some of the primers detect more than one *Mycoplasma* species. These observations were made by evaluating different combinations of PCR primers, specifically, testing for: 1) the number of *Mycoplasma* species that can be detected, 2) primer specificity and 3) background signals and formation of primer dimer without DNA template present.

In some embodiments, some of the primers were designed with modified nucleobase at either the second or third nucleobase from the 3' end of the primer. To illustrate, a primer having the sequence:

(SEQ ID NO: 8)
5' GTAGAGAGTCCTGGAACTCCATGT 3' can have either the "T" or the "G" nucleobase modified. The last 5 nucleobases of the sequence are, . . . CATGT 3'. The first "T", reading left to right is the 3rd nucleobase from the 3' end and the "G" nucleobase (underlined) is the 2nd nucleobase from the 3' end with the final "T" being the 3' terminus base of the primer sequence. For example, the underlined G in SEQ ID NO:8 above can be modified.

Modifications to nucleotides to prevent primer dimer formation are well known to one of skill in the art. Further discussion of nuclease modification to preclude primer dimer formation can be found, for example, in U.S. Pat. Nos. 7,408,051, 7,414,118, 7,517,978, and 7,585,649, each entitled "Modified Oligonucleotides and Applications Thereof," issued to Mullah et al.

In some embodiments, the primers were designed with considerations given to $T_m$, primer dimer interactions, GC content, secondary structure, hybridization strength, and manufacturability. In some embodiments, primers have overlapping regions in a tiered or tandem arrangement which provides reiterative amplification, a re-amplification of an amplification product, to facilitate detection of low copy number *Mycoplasma* sp. nucleic acid targets and accounted for minor species variability to make the multiprimer assay more inclusive for a broad number of *Mycoplasma* species.

In some embodiments of the invention, assays and methods for detecting *Mycoplasma* involve using a plurality of oligonucleotide primers specific for *Mycoplasma* 16S rRNA sequences in an amplification reaction. In certain embodiments, at least 9 such primers are used in the amplification reaction. In some embodiments, the amplification reaction is performed with at least 10, with at least 15, with at least 20, with at least 25, at least 30, at least 31, at least 32, at least 33, at least 34, at least 35, at least 36, at least 37, at least 38, at least 39, or at least 40 such primers. In some embodiments, the amplification reaction is performed with about 10 to about 40, with about 15 to about 40, with about 20 to about 40 such primers, with about 20 to about 35 such primers, with about 20 to about 30 such primers, with about 20 to about 25 such primers, with about 25 to about 40 such primers, with about 25 to about 35 such primers, with about 25 to about 30 such primers, with about 30 to about 40 such primers, with about 30 to about 35 such primers, or with about 35 to about 40 such primers. In some embodiments, the amplification reaction is performed with 9, 10, 15, 20, 25, 30, 31, 32, 33, 34, 35, 36, 37, 38, 39, or 40 such primers.

In some embodiments of the invention, assays and methods for detecting *Mycoplasma* involve using a plurality of oligonucleotide primers selected from the oligonucleotide primers SEQ ID NOs:1-144 in an amplification reaction. In certain embodiments, at least 9 primers selected from SEQ ID NOs: 1-144 are used in the amplification reaction. In some embodiments, the amplification reaction is performed with at least 10, at least 15, at least 20, at least 25, at least 30, at least 31, at least 32, at least 33, at least 34, at least 35, at least 36, at least 37, at least 38, at least 39, or at least 40 primers selected from SEQ ID NOs: 1-144. In some embodiments, the amplification reaction is performed with about 10 to about 40, with about 15 to about 40, with about 20 to about 40, with about 20 to about 35, with about 20 to about 30, with about 20 to about 25, with about 25 to about 40, with about 25 to about 35, with about 25 to about 30, with about 30 to about 40, with about 30 to about 35, or with about 35 to about 40 primers selected from SEQ ID NOs: 1-144. In some embodiments, the amplification reaction is performed with 9, 10, 15, 20, 25, 30, 31, 32, 33, 34, 35, 36, 37, 38, 39, or 40 primers selected from SEQ ID NO:1-144.

In certain embodiments of the invention, the plurality of oligonucleotide primers for use in the assays and methods can include any of the primers SEQ ID NOs: 1-144 and can also exclude any of the primers of SEQ ID NOs: 1-144. In some embodiments, the plurality of oligonucleotide primers comprises primers selected from the primers SEQ ID NOs: 1-144 and also excludes any of the primers of SEQ ID NOs: 1-144. In some embodiments, the plurality of oligonucleotide primers comprises at least 20 primers selected from the primers SEQ ID NOs: 1-144 and further also excludes at least one of the primers of SEQ ID NOs: 1-144.

In some embodiments, the plurality of primers used in the amplification reaction includes at least 13, at least 14, at least 15, at least 16, at least 17, at least 18, at least 19, or at least 20 forward primers. In some embodiments, the plurality of primers used in the amplification reaction includes at least 13, at least 14, at least 15, at least 16, at least 17, at least 18, at least 19, or at least 20 reverse primers. In some embodiments, the plurality of primers used in the amplification reaction includes an equal number of forward and reverse primers. In other embodiments, the plurality of primers used in the amplification reaction includes an unequal number of forward and reverse primers. For example, in some embodiments, the plurality of primers includes a greater number of types of forward primer than the number of types of reverse primer and, in other embodiments, the plurality of primers includes a greater number of types of reverse primer than number of types of forward primer. In some embodiments, the plurality of primers used in the amplification reaction includes at least 15 forward primers and at least 16 reverse primers. In other embodiments, the plurality of primers used in the amplification reaction includes at least 16 forward primers and at least 15 reverse primers. In other embodiments, the plurality of primers used in the amplification reaction includes at least 15 forward primers and at least 15 reverse primers.

As described herein, in certain embodiments, some of the primers in the plurality of primers contain a modified nucleobase to avert primer dimer formation. In some embodiments, at least 5 of the plurality of primers used in the amplification reaction contain a modified nucleobase. In some embodiments, at least 10 of the plurality of primers, at least 15 of the plurality of primers, or at least 20 of the plurality of primers used in the amplification reaction contain a modified nucleobase. In some embodiments, 5 of the primers, 10 of the primers, 15 of the primers, or 20 of the primers used in the amplification reaction contain a modified nucleobase.

In some embodiments, the assay to detect *Mycoplasma* organisms follows the guidelines for *Mycoplasma* sp. detection as established by the U.S. Food and Drug Administration and the European Pharmacopoeia requirements for both sensitivity and specificity. Table 2 comprises a partial list of organisms which made up the Exclusion Panel when developing the disclosed *Mycoplasma* detection assay in order to provide the required specificity. In each reaction listed in Table 2, 10 ng of purified DNA was used in the amplification reaction for each of the excluded organisms with the assays and methods taught herein.

TABLE 2

Exclusion Panel

| Species | Result: Positive/Negative | Tm | Derivative |
|---|---|---|---|
| Human | Negative | n/d | n/d |
| CHO cells | Negative | n/d | n/d |
| Mouse | Negative | n/d | n/d |
| Bacillus cereus | Negative | n/d | n/d |
| Bacillus subtilis | Negative | n/d | n/d |
| Candida albicans | Negative | n/d | n/d |
| Clostridium perfingens | Negative | n/d | n/d |
| Clostridium sporogenes | Negative | n/d | n/d |
| Escherichia coli | Negative | n/d | n/d |
| Lactobacillus delbrueckii | Negative | n/d | n/d |
| Micrococcus luteus | Negative | n/d | n/d |
| Staphylococcus aureus | Negative | n/d | n/d |
| Staphylococcus epidermidis | Negative | n/d | n/d |
| Streptococcus faecalis | Negative | n/d | n/d | n/d, not detected

In some embodiments, the sample comprising the target nucleic acid being analyzed is from a cell culture, a tissue culture, a food sample, an environmental sample, an agricultural sample, a biopharmaceutical sample, a pharmaceutical sample, or water. In some embodiments, nucleic acids are extracted from the sample to be tested and the extracted nucleic acids comprise the test sample in the *Mycoplasma* detection assay.

*Mycoplasma* is a common contaminant of cell and tissue culture samples. The presence of *Mycoplasma* in infected cultures can alter many of the cell's reactions, including altering cell growth rate, inducing morphological changes or cell transformation, and mimicking virus infection. *Mycoplasma*-contaminated cell line is typically significantly influenced in every respect, and, thus, does not comply with Pharmacopoeia and FDA regulatory requirements. Infection is persistent, difficult to detect and diagnose, and very difficult to cure. Therefore, there is an absolute requirement for routine, periodic assays for testing of possible contamination of all cell cultures used in manufacturing of biopharmaceuticals and pharmaceuticals as well as quality control (QC) sampling during manufacturing of biopharmaceuticals and pharmaceuticals. Exisiting methods for identification of *Mycoplasma* contamination rely on traditional bacterial culturing on agarose plates, taking up to 28 days for results. Such a protracted time between sampling and results preclude efficient QC checks, delay production approvals and limit sampling points for QC. PCR-based methods have the greatest potential to become a routine procedure for *Mycoplasma* testing for cell culture, tissue culture, food, environmental, agricultural, biopharmaceutical, and pharmaceutical QC.

In some embodiments, the disclosed teachings provide an assay with a demonstrated ability to detect 1-10 genome copies per mL of sample of *Mycoplasma* DNA with high specificity and efficiency close to 100% and no cross-reactivity with unrelated DNA.

In some embodiments, the present teachings relate to an assay for the detection of *Mycoplasma* that is both sensitive and specific for *Mycoplasma* species and closely related species as required by the European Pharmcopoeia and the U.S. Food and Drug Administration. Detection is measured by a "melt curve" plot. A melt curve as used herein refers to a graphical presentation of an experimental determination of $T_m$. The determination of $T_m$ is well known to one of ordinary skill in the art. For example, the melt curve can be determined following a polymerase chain reaction by heating the population of double-stranded nucleic acid molecules from approximately 60° C. to approximately 90° C. at 0.1 to 1.0 second intervals, and plotting the derivative of the dissociation of the double-stranded nucleic acid verses temperature. The apex of the peak represents the dissociation of half the double-stranded molecules into single strands.

Figure 1B:
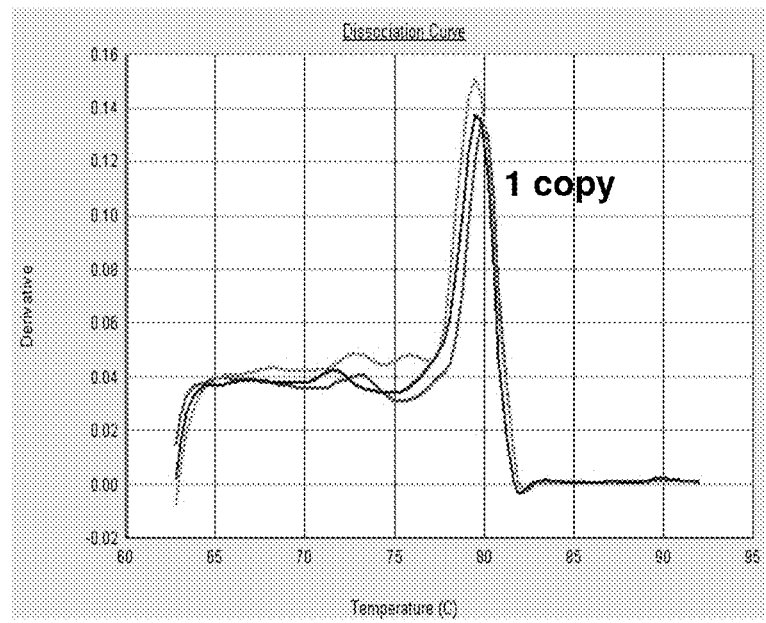
Figure 2A:
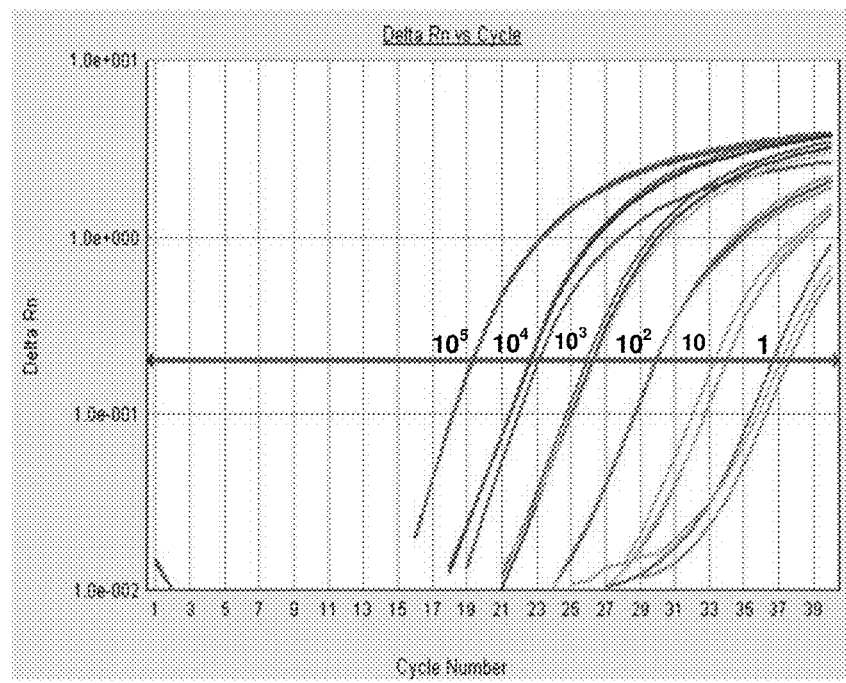
FIGS. 2A-B depicts the sensitivity of the disclosed assay down to 1-10 genome copies/reaction.
Figure 2B:
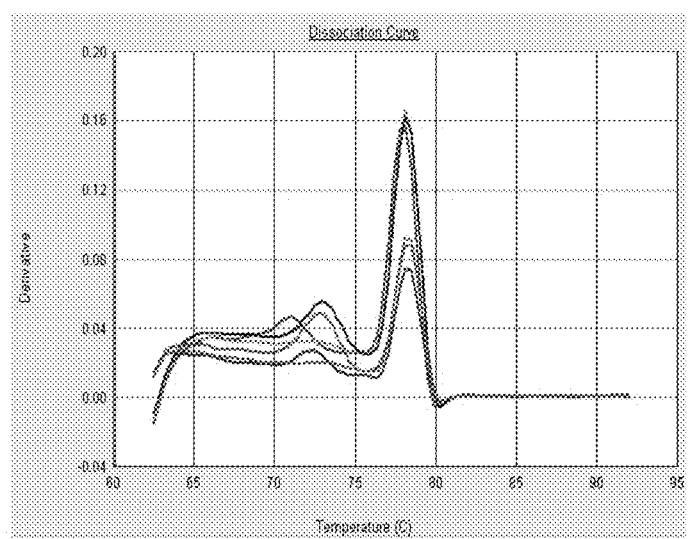

Sensitivity is measured by the lowest limit of detection (LOD). As shown in FIGS. 1A and 1B. The melt curve for *Mycoplasma arginini* indicates a LOD down to a level of <10 genome copies/reaction at a Tm of ~80° C. This result was also achieved with ATCC DNA (data not shown). FIGS. 2A and 2B provides another example of the LOD of the assays of the present teachings, having a LOD of 1-10 copies/reaction at a Tm of ~78° C. In FIG. 2B the uppermost peaks reflect 10 copies/reaction while the lower peaks are for 1 copy/reaction.

Additional examples of the sensitivity of the assay of the present teachings are illustrated in FIGS. 4A-B and Table 3:

TABLE 3

| Organism | LOD (copy/Rx) | Ct | Derivative (at LOD) | Tm (° C.) | PCR Efficiency | R2 |
| --- | --- | --- | --- | --- | --- | --- |
| *Acholeplasma laidlawii* | 10 | ~35 | >0.17 | ~80 | 86 | 0.997 |
| *Mycoplasma arginini* | ~1 | ~34 | >0.13 | ~80 | 97 | 0.998 |
| *Mycoplasma fermentans* | ~1 | ~35 | >0.14 | ~79 | 100 | 0.994 |
| *Mycoplasma gallisepticum* | ~1 | ~35 | >0.17 | ~79 | 99 | 0.998 |
| *Mycoplasma hyopneumoniae* | 10 | ~35 | >0.11 | ~75.5 | 88 | 0.998 |
| *Mycoplasma hyorhinis* | ~1 | 34-36 | >0.12 | ~77.5 | 95 | 0.998 |
| *Mycoplasma orale* | ~1 | ~34-35 | >0.17 | ~79 | 99 | 0.995 |
| *Mycoplasma pirum* | ~1 | 35-36 | >0.13 | ~79 | 100 | 0.998 |
| *Mycoplasma pneumoniae* | 1-10 | ~34 | >0.16 | ~78 | 90 | 0.998 |
| *Mycoplasma salivarium* | ~10 | ~34.5 | ~0.09 | ~76.5 | 92 | 0.999 |
| *Mycoplasma synoviae* | 1-10 | ~35 | >0.16 | ~79 | 100 | 0.984 |
| *Spiroplasma citri* | 10 | ~35 | >0.2 | ~77 | 97 | 0.998 |

In all instances, the LOD was ~1-10 genome copies/reaction with Tm values consistent with a positive assay result as shown in Table 4:

TABLE 4

| Sample Name | Positive/Negative | Tm (° C.) | Derivative |
| --- | --- | --- | --- |
| *Mycoplasma arginini* | Positive | 79.6 | 0.34 |
| *Mycoplasma gallisepticum* | Positive | 79.6 | 0.41 |
| *Mycoplasma orale* | Positive | 79.2 | 0.30 |
| *Mycoplasma hyorhinis* | Positive | 77.4 | 0.34 |
| *Mycoplasma fermentans* | Positive | 78.8 | 0.30 |
| *Mycoplasma pirum* | Positive | 78.8 | 0.40 |
| *Mycoplasma pneumoniae* | Positive | 78.5 | 0.35 |
| *Mycoplasma synoviae* | Positive | 78.8 | 0.30 |
| *Mycoplasma salivarium* | Positive | 77.1 | 0.17 |
| *Mycoplasma hyopneumoniae* | Positive | 75.3 | 0.17 |
| *Acholeplasma laidlawi* | Positive | 79.6 | 0.31 |
| *Spiroplasma citri* | Positive | 77.8 | 0.29 |

In some embodiments, the LOD of the provided assays and methods is less than 100 genome copies per mL of test sample. In some embodiments, the LOD of the assays and methods is less than 10 genome copies per mL of test sample. In some embodiments, the LOD of the assays and methods is less than 1 genome copy per mL of test sample. In some embodiments, the LOD of the provided assays and methods is less than 100 genome copies per PCR reaction. In some embodiments, the LOD of the assays and methods is less than 10 genome copies per PCR reaction. In some embodiments, the LOD of the assays and methods is 1 genome copy per PCR reaction.

In some embodiments, the present teachings relate to an assay with the ability to specifically detect *Mycoplasma* species while excluding detection of host cell species and closely related non-*Mycoplasma* species. Table 2 lists a partial list of host cell species tested by the assay of the current teachings using 10 ng of purified DNA/reaction that are not detected by the claimed assay. No organism on the exclusion list is predicted to cross-hybridize. The absence of an amplification product, i.e., no Tm or Derivative value is evidence that the present assay is specific for *Mycoplasma* species and that the assay fails to detect closely related non-*Mycoplasma* species by PCR.

In some embodiments, the assays and methods of the current teachings for *Mycoplasma* detection provide improved sensitivity and results in as little as five hours. As illustrated in Table 5, a 10-fold dilution series of *Mycoplasma arginini* was prepared and used to spike 13 mL samples of CHO cells ($10^8$ total cells). The nucleic acid (DNA) was purified from each sample using the PrepSEQ™ Sample Preparation Kit+Module M (Applied Biosystems, Foster City Calif.) and analyzed by the assay of the current teachings (for example, Example 1). The colony forming unit (CFU) measurements were determined by standard plate culture of the dilution series.

TABLE 5

| Mycoplasma Spike CFU/mL | Positive/ Negative | $C_T$ | Tm (° C.) | Derivative |
|---|---|---|---|---|
| 0 | Negative | n/a | <75 | <0.04 |
| 0.004 | Negative | n/a | 77 | <0.05 |
| 0.04 | Negative | 38 | 77 | <0.06 |
| 0.4 | Low Level Positive | 35.5 | 78.7 | <0.08 |
| 4 | Positive | 30.6 | 79 | >0.1 |
| ~40 | Positive | 27.6 | 79 | >0.1 |

Clearly, the results indicate the assay of the present teachings has a sensitivity level of at least just 4 CFU/mL in a total preparation and analysis time of about five hours. The assays and methods of the present teachings have an improved level of sensitivity and improved time to results that far exceeds conventional culture methods requiring a minimum of 110-240 CFU/mL and taking up to 28 days to obtain results.

In some embodiments of the invention, the assays and methods for *Mycoplasma* detection provide results in less than 24 hours. In certain embodiments, the assays and methods provide *Mycoplasma* detection results in less than 12 hours, in less than 10 hours, in less than 8 hours, in less than 6 hours, or in 5 hours.

In some embodiments, the assays and methods of the current teachings involve contacting, by for example, but not limited to, hybridization, two or more oligonucleotide primers to a target nucleic acid in a sample. In other embodiments, the target nucleic acid is extracted from the sample prior to contact with two or more oligonucleotide primers. As presented in Examples 1-11, sample preparation and extraction of target nucleic acid utilizing the PrepSEQ™ kit facilitate analyses of a variety of sample types for the presence or absence of *Mycoplasma*, even with samples containing minute quantites of *Mycoplasma*.

In some embodiments, the present teachings relate to an assay for detecting *Mycoplasma* using a variety of detectors including, but not limited to, a nucleic acid dye, a reporter probe, or a reporter probe and a nucleic acid dye. Such dyes and reporters are well known to one of skill in the art, and examples of such are described herein.

In some embodiments, the assays and methods of the present teaching comprise a discriminatory positive control (DPC). A DPC provides both evidence of extraction of the target nucleic acid when added to the sample prior to extraction of target nucleic acid and evidence of fidelity of the PCR reaction both when assayed after extraction and if added as a positive control to the positive control assay vial. Detection of the DPC in the multiprimer PCR reaction can establish confirmation of extraction and PCR reactants. In some embodiments, detection of the DPC amplification product and no detection of the *Mycoplasma* amplification product is a confirmed negative assay for *Mycoplasma*. In other embodiments, detection of both DPC amplification product and *Mycoplasma* amplification product is a confirmed positive assay for *Mycoplasma* in the sample. Further discussion of the DPC can be found in U.S. Patent Application No. 61/163,419, filed Mar. 25, 2009, entitled, "DISCRIMINATORY POSITIVE/EXTRACTION CONTROL DNA," incorporated herein by reference in its entirety.

Figure 3:
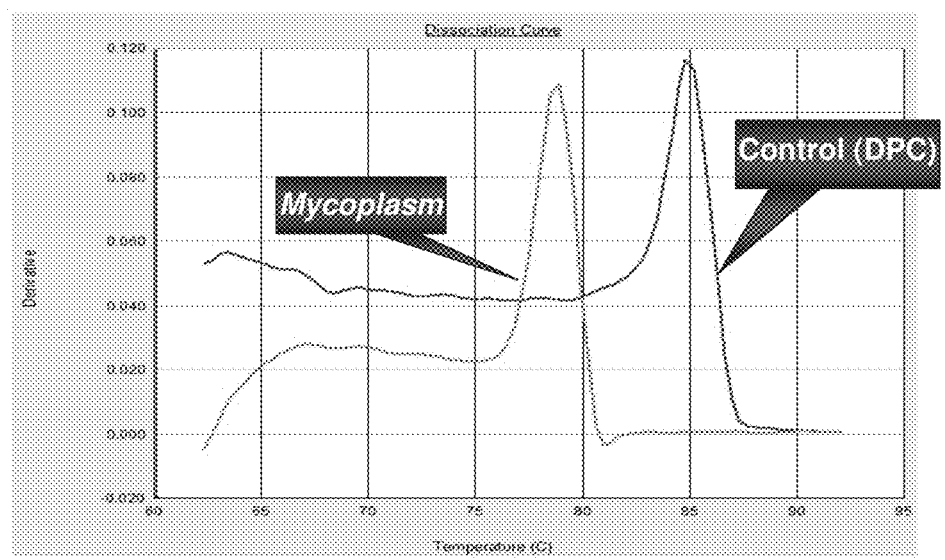
FIG. 3 illustrates the use of a discriminatory positive control (DPC) in conjunction with the present teachings.

In some embodiments, the present teachings relate to an assay for *Mycoplasma* in that an amplification product for a DPC is distinguishable from an amplification product for *Mycoplasma*. In some embodiments, the detection utilizes a plot of the melting temperature for the discriminatory positive control distinguishable from a melting temperature for the *Mycoplasma*. In other embodiments, the detection is by a melt curve for the discriminatory positive control distinguishable from a melt curve for the *Mycoplasma*. As shown in FIG. 3, the Tm in the melt curve for the DPC exceeds that of *Mycoplasma* by about 5° C. Such a difference precludes confusion of an amplification peak for *Mycoplasma* from that for the DPC.

In one aspect, the invention provides assays, methods, and compositions for the detection of *Mycoplasma*, related species and subspecies, and related strains and substrains. In some embodiments, the present assays and methods provide detection of more than 90 *Mycoplasma* species as well as related microorganisms *Acholeplama laidlwaii* and *Spiroplasma citri*. In some embodiments, the present assays and methods can detect over 200 known strains of *Mycoplasma* and related microorganisms such as *Acholeplasma granularum*, *Acholeplasma pieciae* and numerous *Sprioplasma specie*. Table 6 lists the *Mycoplasma* and related microorganisms detectable by the present teachings.

TABLE 6

| | |
|---|---|
| *Acholeplasma granularum* | *Acholeplasma laidlawii**  |
| *Acholeplasma pleciae* | *Mycoplasma alvi* |
| *Mycoplasma anseris* | *Mycoplasma arginini* |
| *Mycoplasma buccale* | *Mycoplasma californicum* |
| *Mycoplasma capricolum* | *Mycoplasma capricolum* subsp. *capricolum* |
| *Mycoplasma capricolum* subsp. *Capricolum* ATCC 27343 | *Mycoplasma capricolum* subsp. *capripneumoniae* |
| *Mycoplasma caviae* | *Mycoplasma equirhinis* |
| *Mycoplasma fermentans* | *Mycoplasma gallinaceum* |
| *Mycoplasma gallisepticum* | *Mycoplasma gallisepticum* R |
| *Mycoplasma gateae* | *Mycoplasma genitalium* |
| *Mycoplasma genitalium* G37 | *Mycoplasma hominis* |
| *Mycoplasma hyorhinis* | *Mycoplasma imitans* |
| *Mycoplasma indiense* | *Mycoplasma mycodies** |
| *Mycoplasma mycodies* subsp. *capri** | *Mycoplasma mycodies* subsp. *mycoides** |
| *Mycoplasma mycodies* subsp. *mycoides* LC* | *Mycoplasma mycodies* subsp. *mycoides* LC str. GM12* |
| *Mycoplasma mycodies* subsp. *mycoides* SC str. PG1* | *Mycoplasma orale** |
| *Mycoplasma phocidae* | *Mycoplasma pirum** |
| *Mycoplasma pneumoniae** | *Mycoplasma pneumoniae* M129* |
| *Mycoplasma salivarium** | *Mycoplasma simbae* |
| *Mycoplasma sp.* | *Mycoplasma sp.* 'bovine group 7' |
| *Mycoplasma sp.* 13CL | *Mycoplasma sp.* PG50 |

TABLE 6-continued

| | |
|---|---|
| Mycoplasma sp. Saalc | Mycoplasma sp. Saale |
| Mycoplasma spumans | Mycoplasma testudinis |
| Mycoplasma timone | Spiroplasma citri* |
| Spiroplasma endosymbiont of Drosophila hydei | Spiroplasma insolitum |
| Spiroplasma kunkelii CR2-3x | Spiroplasma melliferum |
| Spiroplasma phoeniceum | Spiroplasma sp. 277F |
| Spiroplasma sp. CH-1 | Spiroplasma sp. CNA-1 |
| Spiroplasma sp. CNR-1 | Spiroplasma sp. CNR-2 |
| Spiroplasma sp. CR-1 | Spiroplasma sp. Dhd |
| Spiroplasma sp. LB-12 | Spiroplasma sp. M-10 |
| Spiroplasma sp. M10 | Spiroplasma sp. N525 |
| Spiroplasma sp. NSRO | Spiroplasma sp. NSRO-A |
| Mycoplasma adleri | Mycoplasma alkalescens |
| Mycoplasma arthritidis | Mycoplasma auris |
| Mycoplasma bovigenitalium | Mycoplasma bovirhinis |
| Mycoplasma bovoculi* | Mycoplasma buteonis |
| Mycoplasma canadense | Mycoplasma canimucosale |
| Mycoplasma canis | Mycoplasma cloacale |
| Mycoplasma collis | Mycoplasma columbinasale |
| Mycoplasma columbinum | Mycoplasma corogypsi |
| Mycoplasma cottewii | Mycoplasma cricetuli |
| Mycoplasma cynos | Mycoplasma dispar |
| Mycoplasma edwardii | Mycoplasma falconis |
| Mycoplasma faucium | Mycoplasma flocculare |
| Mycoplasma gallopavonis | Mycoplasma glycophilum |
| Mycoplasma gypis | Mycoplasma hyopharyngis |
| Mycoplasma hyopneumoniae* | Mycoplasma hyopneumoniae 232* |
| Mycoplasma hyopneumoniae 7448* | Mycoplasma hyopneumoniae J* |
| Mycoplasma hyosynoviae | Mycoplasma iguanae |
| Mycoplasma lagogenitalium | Mycoplasma lipofaciens |
| Mycoplasma microti | Mycoplasma mobile |
| Mycoplasma mobile 163K | Mycoplasma molare |
| Mycoplasma mustelae | Mycoplasma neurolyticum |
| Mycoplasma ovipneumoniae | Mycoplasma penetrans |
| Mycoplasma penetrans HF-2 | Mycoplasma phocicerebrale |
| Mycoplasma pulmonis | Mycoplasma pulmonis DAB CTIP |
| Mycoplasma sp. 'ovine/caprine serogroup 11' | Mycoplasma sp. 10T4 |
| Mycoplasma sp. 15CL2 | Mycoplasma sp. 8790CV |
| Mycoplasma sp. 94630 | Mycoplasma sp. BHJA |
| Mycoplasma sp. CSL 4779 | Mycoplasma sp. HRC689 |
| Mycoplasma sp. Ms01 | Mycoplasma sp. Ms02 |
| Mycoplasma sp. VJC358 | Mycoplasma subdolum |
| Mycoplasma synoviae* | Mycoplasma synoviae 53* |
| Mycoplasma yeatsii | Mycoplasma zalophi |
| Spiroplasma chrysopicola | Spiroplasma mirum |
| Spiroplasma penaei | Spiroplasma poulsonii |
| Spiroplasma sp. BARC 1357 | Spiroplasma sp. BARC 2649 |
| Spiroplasma sp. BARC 4899 | Spiroplasma sp. CRAB |
| Spiroplasma sp. CRAYFISH | Spiroplasma sp. SHRIMP |
| Spiroplasma sp. TAAS-1 | Spiroplasma syrphidicola |

*Organisms on the European Pharmacopoeia inclusion list.

In some embodiments, disclosed is a multi-primer assay for detecting *Mycoplasma*. In some embodiments, combined in a single vessel is a plurality of oligonucleotide primers selected from SEQ ID NOS:1-144. The primers can contact a sample in the vessel and a PCR amplification reaction is carried out in the vessel, wherein each of the plurality of oligonucleotide primers is present for participation in amplifying the sample to produce an amplification product; and detecting, if present, the amplification product, wherein the presence of an amplification product indicates *Mycoplasma* in the sample.

In some embodiments the vessel can be, for example, a microfuge tube, a 24-, 48-, 96-well plate, a microfluidic-configured plate, a multi-channeled plate or a 396-well plate as would be known to one of skill in the art. Such vessels can be used individually or as part of a robotic or automated sample preparation and analysis system.

In some embodiments of the present teachings the amplification reaction can be a PCR reaction or other amplification reaction as is known to one of skill in the art. The detection of the amplification reaction can be by electrophoresis, radiation, fluorescence or other methods known to one of skill in the art.

In some embodiments of the present teachings disclosed is a method for detecting *Mycoplasma* comprising: combining in a single vessel a plurality of oligonucleotide primers and then introducing a sample to be tested for *Mycoplasma*. The primers can contact a sample in the vessel and a PCR amplification reaction is carried out in the vessel, wherein each of the plurality of oligonucleotide primers is present for participation in amplifying the sample to produce an amplification product; and detecting, if present, the amplification product, wherein the presence of an amplification product indicates *Mycoplasma* in the sample.

In some embodiments of the present teachings disclosed is a method for detecting *Mycoplasma*. In some embodiments the method for detecting *Mycoplasma* comprises extracting nucleic acid from a sample to be tested for *Mycoplasma*; combining in, or adding to, a single vessel a plurality of oligonucleotide primers and then introducing the nucleic acid extracted from the sample to be tested for

*Mycoplasma*. The primers can contact the nucleic acid sample in the vessel and a PCR amplification reaction is carried out in the vessel, wherein each of the plurality of oligonucleotide primers is present for participation in amplifying the sample to produce an amplification product; and detecting, if present, the amplification product, wherein the presence of an amplification product indicates *Mycoplasma* in the sample.

In some embodiments of the present teachings disclosed is a method for detecting *Mycoplasma* comprising: combining in a single vessel a plurality of oligonucleotide primers selected from SEQ ID NOS:1-144 and a sample to be tested for *Mycoplasma*. The primers can contact the sample in the vessel and a PCR amplification reaction is carried out in the vessel, wherein each of the plurality of oligonucleotide primers is present for participation in amplifying the sample to produce an amplification product; and detecting, if present, the amplification product, wherein the presence of an amplification product indicates *Mycoplasma* in the sample.

In some embodiments of the present teachings disclosed is a method for detecting *Mycoplasma*. In some embodiments, the method for detecting *Mycoplasma* comprises extracting nucleic acid from a sample to be tested for *Mycoplasma*; combining in a single vessel a plurality of oligonucleotide primers selected from SEQ ID NOS:1-144 and the nucleic acid extracted from the sample to be tested for *Mycoplasma*. The primers can contact the nucleic acid sample in the vessel and a PCR amplification reaction is carried out in the vessel, wherein each of the plurality of oligonucleotide primers is present for participation in amplifying the sample to produce an amplification product; and detecting, if present, the amplification product, wherein the presence of an amplification product indicates *Mycoplasma* in the sample.

The present teachings are also directed to kits for detection of *Mycoplasma* and closely related species, subspecies, strains and substrains. In some embodiments, the kits utilize methods provided herein are for detection of *Mycoplasma* as required by regulatory bodies or agencies, for example, the US FDA and/or the European Pharmacopoeia. In some embodiments, a kit comprises a container having a plurality of oligonucleotide primers as described herein for use in the methods and assays described herein. In some embodiments, a basic kit can comprise a container having a plurality of oligonucleotide primers selected from the oligonucleotide primers listed in Table 1. A kit can also optionally comprise one or more of a polymerase, dNTPs for strand extension during amplification, loading solution for preparation of the amplified material for electrophoresis, a discriminating positive control nucleic acid, a detectable reporter selected from a nucleic acid dye, a reporter probe or a reporter probe and a nucleic acid dye and a protocol and manual to educate the user and limit error in use.

In certain embodiments of the invention, the kit for *Mycoplasma* detection comprises a container having therein a plurality of oligonucleotide primers selected from the primers of SEQ ID NOs: 1-144. In some embodiments, the plurality of primers in the container includes at least 25, at least 30, at least 31, at least 32, at least 33, at least 34, at least 35, at least 36, at least 37, at least 38, at least 39, or at least 40 primers selected from SEQ ID NOs: 1-144. In some embodiments, the plurality of primers in the container includes 25, 30, 31, 32, 33, 34, 35, 36, 37, 38, 39, or 40 primers selected from SEQ ID NOs: 1-144.

The amounts of the various reagents in the kits also can be varied depending upon a number of factors, such as the optimum sensitivity of the process. It is within the scope of these teachings to provide test kits for use in manual applications or test kits for use with automated sample preparation, reaction set-up, detectors or analyzers.

Those in the art understand that the detection techniques employed are generally not limiting. Rather, a wide variety of detection means are within the scope of the disclosed methods and kits, provided that they allow the presence or absence of an amplicon to be determined.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

EXAMPLES

Example 1

Detection of a Microorganism in a Sample

Nucleic acid samples were prepared from either cultured mammalian cells or from a *Mycoplasma* cell pellet using a PrepSEQ™ *Mycoplamsa* Nucleic Acid Extraction Kit (Applied Biosystems, PN 4401253).

The nucleic acid test samples were amplified in a 30 microliter reaction volume and analyzed as follows. To each tube or reaction well, 18 microliters of PreMix solution comprising 15.0 microliters of Power SYBR® Green PCR Master Mix (2×) and 3.0 microliters of microbe-specific primer pair mix (10×) was added. For a negative control, 12.0 microliters of sterile water was added to the 18 microliters of PreMix. For an inhibition positive control, 2.0-10.0 microliters of the test sample and 2.0 microliters of the discriminatory positive control DNA was added to the 18 microliters of PreMix, and the final volume was adjusted to 30 microliters with water. For a positive control, 2.0 microliters of discriminatory positive control DNA and 20 microliters of sterile water was added to the 18 microliters of PreMix. For the test sample, 2.0-10.0 microliters of test sample was added to the 18 microliters of PreMix, and the final volume was adjusted to 30 microliters with water. The nucleic acid was amplified by PCR and the SYBR® Green dye signal is detected using an Applied Biosystems Real-Time PCR System with a dissociation curve added after the amplification reaction and the associated software. The discriminatory positive control nucleic acid is amplified using the same microbe-specific primer pair as used to test for the microorganisms being evaluated. The PCR conditions used were HOLD: 95° C. for 10 min., 40 cycles at 95° C. for 15 sec, 60° C. for 1 min, and followed by dissociation: 95° C. for 15 sec, 60° C. for 1 min, 95° C. for 15 sec.

Results from an exemplary assay performed with varying concentrations of *Mycoplasma arginini* is shown in FIG. 1. The melt curve indicates a limit of detection (LOD) down to a level of less than 10 genome copies per reaction at a $T_m$ of about 80° C. This same LOD was obtained when the assay was performed with DNA from the ATCC (data not shown).

Results from an exemplary assay performed with a sample containing *Mycoplasma pneumoniae* nucleic acid is shown in FIG. 2. The LOD of this example was 1-10 genome copies per reaction at a $T_m$ of about 78° C. In FIG. 2B, the uppermost peaks reflect 10 copies per reaction while the lower peaks indicate 1 copy per reaction.

FIG. 3 depicts melt curve analysis of a purified *Mycoplasma* DNA sample (10 copies per reaction) and a concurrently run Discriminating Positive Control.

Table 7 provides an exemplary guide for evaluating the amplification and dissociation results of the assay.

TABLE 7

| SYBR® Green dye signal | Derivative target $T_m$ 75 to 85° C. and derivative > 0.1 | Derivative no-target $T_m$ < 75° C. | Result |
| --- | --- | --- | --- |
| Present, $C_T$ < 36 | Present | Absent | Positive |
| Present, $C_T$ < 36 | Present | Present | Positive |
| Present, $C_T$ < 36 | Absent | Present | Presumptive negative |
| Present, but $C_T$ > 36 | Present | Absent | Presumptive positive |
| Present, but $C_T$ > 36 | Present | Present | Presumptive positive |
| Present, but $C_T$ > 36 | Absent | Absent | Presumptive negative |
| Present, but $C_T$ > 36 | Absent | Present | Presumptive negative |
| Absent | Absent | Absent | Negative |
| Absent | Absent | Present | Negative |

FIG. 4 depicts exemplary sensitivity results with 3 samples assayed for *Mycoplasma* DNA. Using Table 7 as a guide, the assay results depicted in FIGS. 4A and 4B indicate that the sample is positive for *Mycoplasma* nucleic acid. The assay results depicted in FIGS. 4C and 4D indicate that this sample is presumptive negative for *Mycoplasma* nucleic acid. The assay results depicted in FIGS. 4E and 4F indicate that this sample is presumptive positive for *Mycoplasma* nucleic acid.

Example 2

Determining the Presence or Absence of a Microorganism in a Liquid Food Sample

Twenty-five milliliters (mL) of a milk sample are added to a nonfiltered stomacher bag (e.g., a 15 cm×23 cm Whirl-Pak bag, #B01196WA, Nasco, Fort Atkinson, Wis.) containing 225 mL brain heart infusion broth (BHI) culture medium. The inoculated medium in the stomacher bag is incubated at 37° C. on a rotating platform set at about 125 rpm for an appropriate time, e.g., 5-6 hours to enrich the microorganisms of interest. The enriched medium is transferred to centrifuge bottles and centrifuged in a Beckman Alegra 25R centrifuge for 15 minutes at 8,000 rpm. The supernatant is decanted and the centrifuge bottles are inverted to drain the residual supernatant. Excess fat is removed with sterile gauze (e.g., ITW Texwipe, # TX708A). The pellets in the drained centrifuged bottles are resuspended in about 1.0 mL PBS, transferred to a 1.5 mL microcentrifuge tube, and 20 µL Dynal Magnetic beads (Dynal Biotech LLC; beads with antibodies that specifically bind *Salmonella, E. coli* 0157: H7, or *Listeria* are commercially available) are added to the 1 mL suspension. The beads are concentrated using a magnet, the supernatant is aspirated, and the beads are washed twice with PBST (PBS containing 0.05% Tween 20), according to the manufacturer's "Manual Method" instructions. The final bead pellet is resuspended in 10 µL nuclease-free distilled water and the entire volume is added to the amplification reaction composition. The nucleic acid in the resuspended pellet is amplified and analyzed as described in MicroSEQ™ *Mycoplasma* Real-Time PCR Detection Kit (P/N 4393111, Applied Biosystems) to determine the presence or absence of the microorganism of interest in the sample.

Example 3

Determining the Presence or Absence of a Microorganism in a Solid Food Sample

Twenty-five grams of a ground beef sample are added to a filtered stomacher bag (e.g., a 15 cm×23 cm filtered Whirl-Pak bag, #B01348WA, Nasco, Fort Atkinson, Wis.) and the weight adjusted to 250 g using brain heart infusion broth (BHI) as the culture medium. The inoculated medium is homogenized using a stomacher laboratory blender (e.g., GSR Technical Sales, Edmonton, AB, Canada; or AGB Scientific Ltd., Dublin, Ireland) for about 60 seconds at normal speed. The stomacher bag is incubated at 37° C. on a rotating table set at about 125 rpm to enrich the microorganisms of interest. The enriched medium is first filtered using perlite, as described in Example 2. The filtrate is filtered a second time through a 5 micron filter (e.g., a Durapore membrane in a filtration assembly, Millipore Corp.) and the second filtrate is then filtered through a 0.45 micron filter (e.g., a Durapore membrane, Millipore Corp.). The 0.45 micron filter is removed and transferred to a sterile 50 mL polypropylene tube containing 20 mL BHI medium. The tube is vortexed for about three minutes to dislodge the microorganisms from the surface of the membrane filter. The membrane is removed from the tube, ten microliters of Glycoblue (Ambion, Austin Tex.) co-precipitant and between 10 µL and 50 µL of discriminatory positive control is added to the tube to confirm nucleic acid extraction, and the tube is centrifuged at 8,000 rpm for 15 minutes to pellet the microorganisms. The supernatant is aspirated and the pellet is resuspended in 10 µL sterile water. The nucleic acid in the resuspended pellet is amplified and analyzed as described in Example 2 to determine the presence or absence of the microorganism of interest in the food sample.

Example 4

Determining the Presence or Absence of a Microorganism in a Water Sample

One liter of a water sample is filtered through a 0.22 micron filter in a filtration assembly. The membrane is transferred to a suitable incubation vessel containing 90 mL of tryptic soy broth and vigorously shaken or vortexed for three minutes to dislodge the bacteria trapped on the surface of the filter. The filter is removed from the incubation vessel and the inoculated medium is incubated for about 6 hours at 37° C. on a rotary shaker at about 80 rpm. The enriched medium is transferred to two sterile 50 mL conical centrifuge tubes, 20 μL of Glycoblue is added to each tube, between 10 μL and 50 μL of discriminatory positive control is added to only one tube and the tubes are centrifuged at 8000 rpm for 15 minutes. The supernatant is aspirated and the pellet is resuspended in 10 μL nuclease-free distilled water. The nucleic acid in the resuspended pellet is amplified and analyzed as described in Example 1 to determine the presence or absence of the microorganism of interest in the water sample.

Example 5

Determining the Presence or Absence of a Microorganism in a Biopharmaceutical or Pharmaceutical Sample by Use of a Nucleic Acid Dye Samples are prepared according to the PrepSEQ™ Ultra Sample Preparation Reagent Protocol (PN 4367554) or the PrepSEQ™ *Mycoplasma* Nucleic Acid Extraction Kit Protocol (PN 4401253) (both from Applied Biosystems). To each labeled tube or reaction well add 18 μL of PreMix solution comprising 15.0 μL Power SYBR® Green PCR Master Mix (2×) and 3.0 μL microbe-specific primer pair mix (10×). For the negative control add 12.0 μL sterile water (negative control); for the inhibition positive control add 2.0-10.0 μL test sample and 2.0 μL discriminatory positive control DNA, adjusting the final volume to 30 μL; for the positive control add 2.0 μL discriminatory positive control DNA and 20 μL sterile water; and for the test sample add 2.0 μL sample and 10.0 μL sterile water. The nucleic acid is amplified by PCR and the SYBR® Green dye signal is detected using an Applied Biosystems Real-Time PCR System with a dissociation curve added after the amplification reaction and the associated software. The discriminatory positive control nucleic acid is amplified using the same microbe-specific primer pair as used to test for the microorganisms being evaluated. PCR conditions, HOLD: 95° C., 10 min., 40 cycles at 95° C., 15 sec, 60° C., followed by dissociation: 95° C., 15 sec. 60° C., 1 min and 95° C., 15 sec. or refer to the instrument's dissociation-curve setup for information on running the dissociation-curve program.

Example 6

Determining the Presence or Absence of a Microorganism in a Solid Food Sample by Use of a Nucleic Acid Dye Follow the sample preparation and extraction method as described in Example 3 and set up the amplification and dissociation reactions as described in Example 5 to determine the presence or absence of the microorganism of interest in the solid food sample.

Example 7

Determining the Presence or Absence of a Microorganism in a Liquid Food Sample by Use of a Nucleic Acid Dye Follow the sample preparation and extraction method as described in Example 2 and set up the amplification and dissociation reactions as described in Example 5 to determine the presence or absence of the microorganism of interest in the liquid food sample.

Example 8

Determining the presence or Absence of a Microorganism in a Water Sample by Use of a Nucleic Acid Dye Follow the sample preparation and extraction method as described in Example 4 and set up the amplification and dissociation reactions as described in Example 5 to determine the presence or absence of the microorganism of interest in the water sample.

Example 9

Determining the Presence or Absence of a Microorganism in an Environmental Sample by Use of a Nucleic Acid Dye Follow the sample preparation and extraction methods and set up the amplification and dissociation reactions as described in Example 5 to determine the presence or absence of the microorganism of interest in the environmental sample.

Example 10

Determining the Presence or Absence of a Microorganism in an Agricultural Sample by Use of a Nucleic Acid Dye Follow the sample preparation and extraction methods and set up the amplification and dissociation reactions as described in Example 5 to determine the presence or absence of the microorganism of interest in the agricultural sample.

Example 11

Designing a Discriminating Positive Control

The discriminating positive control template (DPC) is a double stranded synthetic DNA molecule consisting of an internal "stuffer" fragment flanked by binding sites for two specific TaqMan® assay primers. The 5' to 3' strand is indicated a "X" and the complementary, 3' to 5' reverse strand is indicated by "Z" in the illustration below. The stuffer fragment is indicated by "SSSS . . . SSS" and the primer-binding sites are underlined "XXXX...XXX" (forward primer, Primer 1) and underlined "ZZZZ...ZZZ" (reverse primer, Primer 2). When included in a TaqMan assay, the assay primers facilitate amplification of the DPC. In general, the stuffer fragment was between as few as 8 nucleotides in length and up to 40 nucleotides in length, not accounting for the length of the primers flanking the stuffer fragment. Selection of the stuffer fragment was based on high % GC rich regions of the microorganism of interest or of a naturally occurring high % GC genome region but not necessarily polymorphic repeat regions, as would be understood by one of skill in the art. Basing the stuffer fragment on a naturally occurring nucleotide sequence assured that the sequence was easily replicated by DNA polymerase.

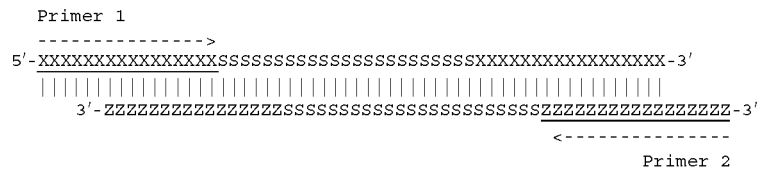

Determination of Melting Temperature ($T_m$)

The $T_m$ of the DPC is influenced by the length and nucleotide composition of the DPC sequence. Because DNA melting is a complex reaction that is highly sequence-specific, even subtle changes in the primer binding sites or stuffer nucleotide sequence can have a significant effect on the DPC $T_m$. Additionally, the concentration of monovalent (e.g., $Na^+$) and divalent (e.g., $Mg^{2+}$) cations also effects $T_m$. Each of these cations is found within the TaqMan reaction mix used in TaqMan qPCR assays. The $T_m$ prediction algorithm, OligoAnalyzer (Integrated DNA Technologies, Inc. (Coralville, Iowa)), was used to predict the calculated DPC $T_m$, and accounted for cation concentration when calculating $T_m$. Because $T_m$ prediction algorithms have been optimized for short DNA sequences (up to about 25 bp, the length range of typical oligonucleotide primers), the $T_m$ prediction of longer sequences was not as accurate. Therefore, testing of between ten and around thirteen DPCs with the desired $T_m$ value were designed and then tested empirically to determine actual $T_m$ (data not shown). Designing of the nucleotide primer-binding site sequences In general, the DPC began with the forward primer sequence and ended with the reverse complement of the reverse primer sequence. However, when using more than two amplification primers, the DPC was designed to have only one forward and one reverse primer-binding site. The primer-binding sites were identical to or very close to identical to the primer-binding sites of the microorganism of interest. In order to obtain double stranded amplicons with elevated $T_m$, GC-rich sequences were inserted between the primer binding sites.

Designing of the "Stuffer Fragment" Nucleotide Sequence

The stuffer fragment can be omitted depending upon the $T_m$ of the DPC in relation to the $T_m$ of the amplicon of the microorganism of interest. The minimal DPC had no stuffer, just two primer binding sites. The length of the stuffer fragment was changed to influence the $T_m$. Increasing the length of the stuffer from 8 bp to 30 bp for a pure GC sequence resulted in a 3° C. increase in $T_m$ with an almost linear response. Increasing the length of a pure GC stuffer beyond 30 bp was found to have a negligible effect on $T_m$. When a longer DPC was desired, a GC-rich stuffer of the desired length was inserted between the primer binding sites. If the resulting $T_m$ of the resulting DPC was too high, the $T_m$ was adjusted by changing a fraction of the G and C bases to A and/or T. For a DPC with a 50 bp internal stuffer, the $T_m$ can be modulated over a 2° C. range by changing from 4 to 11 C and G bases to A and/or T.

Cloning of the Discriminating Positive Control

The resulting DPCs selected had a $T_m$ of between 82° C. to 85° C., good PCR efficiency and strong signal level (the derivative seen in the $T_m$ curve, data not shown). The selected DPCs were cloned into a DNA vector and can be subsequently cloned into a larger vector (having a size of around 12 Kb). It is known that plasmid DNA is not recovered as efficiently as higher molecular weight DNA when using the PrepSeq™ Kits. Therefore the DPC can be cloned into, for example but not limited too Bacteriophage Lambda (genome size approx. 55 Kb), increasing molecular weight of the DPC. Recovery is only of concern if the assay is quantitative. So long as the nucleic acid of the DPC is recovered and detected in a polymerase chain reaction, it serves as a discriminatory positive control.

Those in the art will appreciate that these illustrative examples are not limiting and that a variety of combinations of suitable culture media, incubation times, concentration methods, including without limitation, different filtration media, nucleic acid extraction procedures, amplification techniques and detection methods can be employed within the scope of the current teachings. Those in the art will understand that the person of ordinary skill, informed by the current teachings, can determine the presence or absence of a microorganism of interest in a wide variety of food samples, water samples, agricultural samples, environmental samples, biopharmaceutical and pharmaceutical samples, or suitable clinical samples, typically in about 12 hours or less and often in a single work day.

The assays, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

The foregoing examples are for illustration purposes and are not intended to limit the scope of the teachings herein. Although the disclosed teachings have been described with reference to various applications, methods, assays, and kits, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

What is claimed is:

1. A multi-primer assay for detecting *Mycoplasma* in a sample, comprising:

a.) contacting the sample with the plurality of oligonucleotide primers selected from the group consisting of SEQ ID NOs:1-144 in a single vessel;

b.) performing a multi-primer amplification reaction in the vessel in the presence of a nucleic acid dye or a dye probe, wherein each of the plurality of oligonucleotide primers is present for participation in amplifying a target nucleic acid in the sample to produce an amplification product comprising the nucleic acid dye or the dye probe; and c.) detecting a signal from the nucleic acid dye or the dye probe of the amplification product, wherein the presence of an amplification product indicates *Mycoplasma* in the sample;

wherein the assay is capable of detecting more than 90 *Mycoplasma* species or related microorganisms *Acholeplama laidlwaii* and *Spiroplasma citri*.

2. The assay according to claim 1, wherein at least one of the plurality of oligonucleotide primers comprises a modified nucleobase at the third or fourth nucleobase from the 3' end of the primer.

3. The assay of claim 1 wherein the plurality of primers comprises at least 15 forward primers and at least 16 reverse primers.

4. The assay according to claim 1, wherein the plurality of oligonucleotide primers comprises at least twenty oligonucleotide primers.

5. The assay according to claim 1, wherein the sample comprises either a cell culture, a tissue culture, a food sample, an environmental sample, an agricultural sample, a biopharmaceutical sample, a pharmaceutical sample, or water.

6. The assay according to claim 1, wherein the contacting comprises hybridizing one or more of the oligonucleotide primers to a target nucleic acid in the sample.

7. The assay according to claim 6, wherein the target nucleic acid is extracted from the sample prior to hybridizing with the one or more oligonucleotide primers.

8. The assay according to claim 1, wherein the detecting comprises a detector selected from the group consisting of a nucleic acid dye, a reporter probe, or a reporter probe and a nucleic acid dye.

9. The assay according to claim 1, wherein the assay comprises a discriminatory positive control (DPC) nucleic acid.

10. The assay according to claim 9, wherein the DPC nucleic acid is added to the sample prior to extraction of the target nucleic acid of the sample.

11. The assay according to claim 10, wherein the DPC nucleic acid is extracted simultaneously with the target nucleic acid of the sample.

12. The assay according to claim 11, wherein the DPC nucleic acid is amplified in the multi-primer amplification reaction and the DPC amplification product is detected.

13. The assay according to claim 12, wherein the detecting comprises a melting temperature for the discriminatory positive control distinguishable from a melting temperature for the *Mycoplasma*.

14. The assay according to claim 13, wherein detection of the DPC amplification product and no detection of the *Mycoplasma* amplification product is a confirmed negative assay for *Mycoplasma*; wherein detection of the DPC amplification product and detection of the *Mycoplasma* amplification product is a confirmed positive assay for *Mycoplasma*.

15. A method for detecting *Mycoplasma* comprising:
   a.) extracting nucleic acid from a sample to be tested for *Mycoplasma*;
   b.) combining in a single vessel a plurality of oligonucleotide primers and the nucleic acid from the sample;
   c.) contacting the nucleic acid from the sample with the plurality of oligonucleotide primers in the vessel, said oligonucleotide primers selected from the group consisting of SEQ ID NOS:1-144;
   d.) performing a multi-primer amplification reaction in the vessel, wherein each of the plurality of oligonucleotide primers is present for participation in amplifying the sample to produce an amplification product; and
   e.) detecting the amplification product, wherein the presence of the amplification product indicates *Mycoplasma* in the sample;

wherein the assay can detect more than 90 *Mycoplasma* species or related microorganisms *Acholeplama laidlwaii* and *Spiroplasma citri*.

16. The method for detecting *Mycoplasma* of claim 15 comprising:
   a.) optionally, combining a discriminating positive control (DPC) nucleic acid with the sample to be tested for *Mycoplasma*;
   b.) extracting nucleic acid from the combined sample and DPC.

17. The method for detecting *Mycoplasma* of claim 15, wherein a DPC nucleic acid is added to the vessel.

18. The method for detecting *Mycoplasma* of claim 17, wherein the DPC nucleic acid is amplified in the multi-primer amplification reaction and the DPC amplification product is detected.

19. The method for detecting *Mycoplasma* of claim 18, wherein the detecting comprises a melting temperature for the discriminatory positive control distinguishable from a melting temperature for the *Mycoplasma*.

* * * * *